(12) United States Patent
Miyake et al.

(10) Patent No.: US 11,306,055 B2
(45) Date of Patent: Apr. 19, 2022

(54) ISOCYANATE PRODUCTION METHOD

(71) Applicant: ASAHI KASEI KABUSHIKI KAISHA, Tokyo (JP)

(72) Inventors: Nobuhisa Miyake, Tokyo (JP); Yuji Kosugi, Tokyo (JP); Yusuke Sakurai, Tokyo (JP); Masaaki Shinohata, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 92 days.

(21) Appl. No.: 16/612,790

(22) PCT Filed: May 15, 2018

(86) PCT No.: PCT/JP2018/018822
§ 371 (c)(1),
(2) Date: Nov. 12, 2019

(87) PCT Pub. No.: WO2018/212206
PCT Pub. Date: Nov. 22, 2018

(65) Prior Publication Data
US 2020/0216387 A1 Jul. 9, 2020

(30) Foreign Application Priority Data
May 15, 2017 (JP) .............................. JP2017-096777

(51) Int. Cl.
*C07C 263/04* (2006.01)

(52) U.S. Cl.
CPC ................. *C07C 263/04* (2013.01)

(58) Field of Classification Search
CPC .................................................. C07C 263/04
USPC ......................................................... 558/313
See application file for complete search history.

(56) References Cited

U.S. PATENT DOCUMENTS

| | | | |
|---|---|---|---|
| 3,992,430 A | 11/1976 | Bacskai | |
| 4,081,472 A | 3/1978 | Tsumura et al. | |
| 4,097,676 A | 6/1978 | Romano | |
| 4,659,845 A | 4/1987 | Rivetti et al. | |
| 8,895,774 B2 * | 11/2014 | Shinohata | C07C 263/04 560/345 |
| 2003/0125579 A1 | 7/2003 | Yoshida et al. | |
| 2007/0015932 A1 | 1/2007 | Fujita et al. | |
| 2011/0054211 A1 | 3/2011 | Shinohata et al. | |

FOREIGN PATENT DOCUMENTS

| | | |
|---|---|---|
| CN | 102026964 A | 4/2011 |
| CN | 103864810 A | 6/2014 |
| DE | 925496 | 3/1955 |
| EP | 0 449 558 A2 | 10/1991 |
| EP | 0 902 014 A1 | 3/1999 |
| EP | 2 774 915 A1 | 9/2014 |
| JP | 52-71443 | 6/1977 |
| JP | 52-136147 A | 11/1977 |
| JP | 61-183257 A | 8/1986 |
| JP | 01-230550 A | 9/1989 |
| JP | 02-174751 A | 7/1990 |
| JP | 3-275662 A | 12/1991 |
| JP | 06-192207 A | 7/1994 |
| JP | 07-509461 A | 10/1995 |
| JP | 08-157431 A | 6/1996 |
| JP | 10-316645 A | 12/1998 |
| JP | 2003-252846 A | 9/2003 |
| JP | 2004-262834 A | 9/2004 |
| JP | 2007-22932 A | 2/2007 |
| WO | 94/02450 A1 | 2/1994 |
| WO | 2009/139061 A1 | 11/2009 |

OTHER PUBLICATIONS

European Search Report issued in European Patent Application No. 18801582.0 dated Apr. 22, 2020.
Kim et al. "In vitro solubility, stability and permeability of novel quercetin-amino acid conjugates," Bioorganic & Medicinal Chemistry, vol. 17, No. 3, 2009, pp. 1164-1171.
Sanda et al. "Syntheses of Isocyanates by Thermal Decomposition of Carbamates," Nihon Setchaku Gakkaishi, vol. 33, No. 5, 1997, pp. 175-180.
Frick et al., Carbonate Couplers and Functional Cyclic Carbonates from Amino Acids and Glucosamine, Macromolecular Chemistry and Physics, 210, pp. 242-255, 2009.
Hoffmann, "On the Aromatic Cyanates", Berlin University Laboratory, Berichte der Deutechen Chemischen Gesellschaft, vol. 3, p. 653-658, 1870.
Yamazaki et al., "The Reaction of Diphenyl Carbonate with Amines and Its Application to Polymer Synthesis," Journal of Polymer Science: Polymer Chemistry Edition, vol. 17, pp. 835-841, 1979.
International Search Report issued in International Application No. PCT/JP2018/018822 dated Aug. 7, 2018.
Written Opinion of the International Searching Authority issued in International Application No. PCT/JP2018/018822 dated Aug. 7, 2018.

\* cited by examiner

*Primary Examiner* — Kristin A Vajda
(74) *Attorney, Agent, or Firm* — Morgan, Lewis & Bockius LLP

(57) ABSTRACT

An isocyanate production method is characterized by having: a carbamation step in which a carbonic acid ester, an inorganic acid salt of an amino acid derivative, and a basic compound are reacted to obtain a reaction mixture containing a carbamic acid ester derived from the carbonic acid ester, a hydroxy compound derived from the carbonic acid ester, and the carbonic acid ester; and a thermal decomposition step in which the carbamic acid ester is subjected to a thermal decomposition reaction to obtain an isocyanate.

18 Claims, 4 Drawing Sheets

ISOCYANATE PRODUCTION METHOD

TECHNICAL FIELD

The present invention relates to an isocyanate production method.

The present invention claims priority on the basis of Japanese Patent Application No. 2017-096777 filed in Japan on May 15, 2017, the contents of which are incorporated herein by reference.

BACKGROUND OF THE INVENTION

An isocyanate is widely used as a raw material to prepare a polyurethane foam, a coating material, an adhesive agent or the like. The major industrial production method of an isocyanate is a method in which an amine compound and a phosgene are reacted (phosgene method), and almost all global production is produced by the phosgene method. However, the phosgene method causes many problems.

As the first problem, a large amount of phosgene is used as a starting material. Phosgene has excessively high toxicity, and therefore requires particular attention to prevent exposure thereof to engaged persons, as well as particular devices to remove wastage.

As the second problem, a large amount of hydrogen chloride having high corrosiveness is produced as a by-product, and therefore a process to remove the hydrogen chloride is required. In addition, the resultant isocyanate often contains hydrolyzable chlorine. Accordingly, there is a case where the use of the isocyanate produced by the phosgene method causes adverse effects on the weather-resistance or the heat-resistance of polyurethane products.

In view of such a background, a production method of an isocyanate compound in which no phosgene is used has been desired. As one of the production methods of an isocyanate compound in which no phosgene is used, a method in which a carbamic acid ester is subjected to thermal decomposition has been proposed. It is conventionally known that the thermal decomposition of the carbamic acid ester produces an isocyanate and a hydroxy compound (see, for example, Non-Patent Document 1). The basic reaction is illustrated by the following formula.

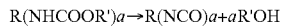   (1)

In the formula, R represents an organic residual group having a valency of a, R' represents a monovalent organic residual group, and a represents an integer of 1 or more.

Among carbamic acid esters, a carbamic acid ester in which an ester group is an aromatic group has the advantage of being able to decrease the temperature at the thermal decomposition reaction in comparison with an alkyl carbamate in which an ester group is an alkyl group (see Patent Document 1).

Various method have been disclosed until now as a method for producing the carbamic acid ester.

Patent Document 2 discloses that an alkyl monoamine and a diaryl carbonate are reacted in the presence of a solvent such as benzene, dioxane, or carbon tetrachloride, to obtain a corresponding alkyl monocarbamate at a yield of 90% to 95%.

In addition, Patent Document 3 discloses a method in which phenyl methylcarbamate is prepared continuously from methylamine and diphenyl carbonate.

However, these methods are methods for producing alkyl carbamates using lower alkyl monoamines as amines, but are not methods for producing an alkyl polycarbamate.

In the case where a corresponding alkyl polycarbamate is prepared from an alkyl polyamine such as an alkyl diamine or an alkyl triamine, there are problems which are quite different from those caused when an alkyl monoamine is used.

In addition to the reaction of formula (2), only side reactions of formula (3) and/or formula (4) causes urea compounds as by-products, in the case where an alkyl monoamine is used, but very many kinds of urea compounds such as compounds of formula (5), (6), and/or (7), are generated as by-products in the case where an alkyl polyamine, such as alkyl diamine or alkyl triamine, is used.

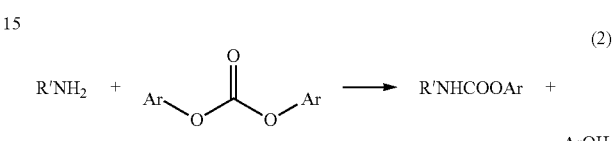

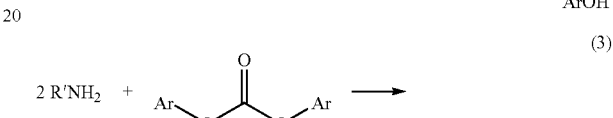

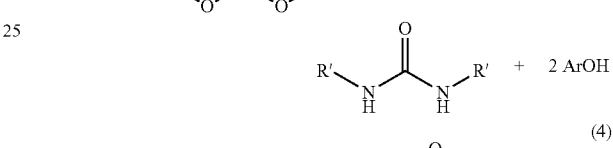

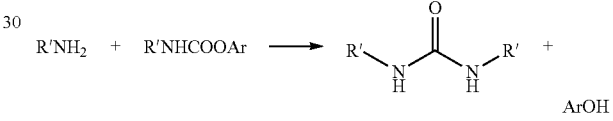

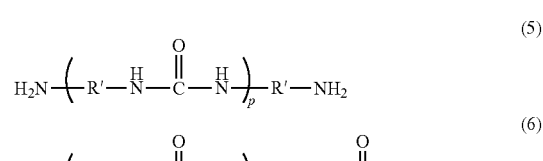

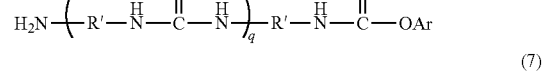

In the formulae, R' represents a monovalent alkyl group or aromatic group, Ar represents a monovalent aromatic group, and p, q, and r, each represent an integer of 1 or more.

In other words, there are a problem in which the yield of an alkyl polycarbamate, which is a target compound, is decreased by side reactions of these various kinds of urea compounds, and a problem in which it is very difficult to separate and purify the target compound from a mixture containing these urea compounds or polyurea compounds.

Thus, there have been very few attempts in which an alkyl polycarbamate is obtained from an alkyl polyamine and a diaryl carbonate. As the few reported instances, Patent Document 4 proposes a method in which a 1,6-hexamethylene dicarbamic acid phenyl ester is obtained by adding dropwise a solution in which 1 mol of 1,6-hexamethylene diamine is dissolved in 5 fold quantity of benzene into a solution in which 1 mole of diphenyl carbonate is dissolved in 5 fold quantity of benzene while conducting stirring at 80° C. to allow the reaction to proceed. According to Patent Document 4, it is important to use a solvent which does not allow the resultant 1,6-hexamethylene dicarbamic acid phenyl ester to be dissolved therein, as possible, as a reaction solvent, so as to allow the reaction to proceed advantageously, and it is disclosed that, as such a solvent, hydrocarbons such as benzene or chlorobenzene are preferable.

From such a viewpoint, according to Non-Patent Document 2, a target 1,6-hexamethylene dicarbamic acid phenyl ester is obtained by reacting 0.01 mol of diphenyl carbonate and 0.005 mol of 1,6-hexamethylene diamine using 40 mL of toluene as a reaction solvent to allow the reaction to proceed for a long time of 20 hours. However, the yield thereof is 93% even by the use of such a large amount of toluene, and there is a problem in which a urea compound or a polyurea compound which have to be separated are generated as by-products.

In addition, Patent Document 5 discloses a method for producing a diurethane compound in which a diaryl carbonate and an amine compound are reacted in the presence of a protic acid. However, the yield of the diurethane compound is not sufficient to conduct industrially the production method disclosed by Patent Document 5, and there is a defect in which the reaction has to be conducted at a low temperature to suppress the side reaction, and thus the reaction time elongates.

Patent Document 6 discloses a method for reacting a diaryl carbonate and an aromatic polyamine in the presence of a heterocyclic tertiary amine such as 2-hydroxy pyridine. The method has a problem in which equimolar or more of an expensive catalyst, relative to the reaction substrate, is required, and the reaction speed is low.

Patent Document 7 discloses a method in which an aromatic amine and a diaryl carbonate are reacted in the presence of a Lewis acid catalyst at 140° C. to 230° C. to synthesize an aromatic urethane. However, the method has also problems in which the use of the Lewis acid causes corrosion of an apparatus and the separation and collection of resultant products are difficult.

Patent Document 8 discloses a method for producing an alkyl polycarbamate by reacting an alkyl polyamine and a diaryl carbonate using: the diaryl carbonate in an amount of 1 to 3 equivalents per equivalent of amino group of the alkyl polyamine; and an aromatic hydroxy compound as a reaction solvent, to allow the reaction to proceed in a substantially uniformly dissolved state.

According to the patent document, the alkyl polycarbamate is obtained at a high yield, usually 96% or more, preferably 98% or more, with a high selection rate.

However, the synthesis of a urea compound is confirmed, although the amount thereof is very low, and therefore there is a problem in which the synthesis of the urea compound is not completely inhibited.

In addition, a method in which a carbamic acid ester is synthesized using a dicarbonate instead of a carbonic acid ester has been disclosed. For example, Patent Document 9 discloses a method for preparing a carbamate by reacting a diester carbonate and an amine in a liquid phase in the presence of at least 1% by mol of water.

Polyamines have also been studied, and, for example, Patent Document 10 discloses a method for preparing a carbamic acid ester using a dicarbonate and an amino group of an amino acid, or a compound derived from an amino acid, such as an amino acid ester.

In addition, Patent Document 11 proposes a method for preparing a carbamic acid ester by reacting an alkyl aryl carbonate and an amino acid, for example.

DOCUMENTS OF RELATED ART

| Patent Documents | |
|---|---|
| Patent Document 1: | U.S. Pat. No. 3,992,430 |
| Patent Document 2: | Japanese Unexamined Patent Application Publication No. Sho 52-71443 |
| Patent Document 3: | Japanese Unexamined Patent Application Publication No. Sho 61-183257 |
| Patent Document 4: | German Patent No. 925496 |
| Patent Document 5: | Japanese Unexamined Patent Application Publication No. Hei 10-316645 |
| Patent Document 6: | Japanese Unexamined Patent Application Publication No. Sho 52-136147 |
| Patent Document 7: | Japanese Unexamined Patent Application Publication No. 2004-262834 |
| Patent Document 8: | Japanese Unexamined Patent Application Publication No. Hei 1-230550 |
| Patent Document 9: | Japanese Unexamined Patent Application Publication No. Hei 3-275662 |
| Patent Document 10: | Japanese Unexamined Patent Application Publication No. Hei 6-1092207 |
| Patent Document 11: | Japanese Unexamined Patent Application Publication No. 2003-252846 |
| Non-Patent Documents | |
| Non-Patent Document 1: | Berchte der Deutechen Chemischen Gesellschaft, volume 3, page 653, 1870 |
| Non-Patent Document 2: | Journal of Polymer Science Polymer Chemistry Edition, volume 17, page 835, 1979 |

SUMMARY OF THE INVENTION

Problems to be Solved by the Invention

Although several methods for preparing an isocyanate by preparing a carbamic acid ester form a polyamine, followed by conducting thermal decomposition have been disclosed, the problems remain in the methods. In addition, the general idea of polyurethane derived from plants (bio polyurethane) has been proposed in recent years from the viewpoint of environmental issues and global heating, but a method for producing an isocyanate from plant-derived components to realize bio-polyurethane, particularly an isocyanate from an amino acid, without using phosgene, has not been disclosed.

The present invention aims to provide a method for preparing an isocyanate from a plant-derived component, particularly an isocyanate from an amino acid, using a carbonic acid ester as a raw material, a method for preparing an intermediate thereof, particularly a method for preparing a carbamic acid ester using a carbonic acid ester and an inorganic acid salt of an amino acid derivative, and a method for preparing an isocyanate using the carbamic acid ester.

Means to Solve the Problems

The present invention encompasses the following aspects.

[1] A production method of a carbamic acid ester derived from a carbonic acid ester, containing supplying the carbonic acid ester, an inorganic acid salt of an amino acid derivative, and a basic compound to a carbamation reactor to allow reaction to proceed.

[2] The production method of a carbamic acid ester according to [1], wherein the amino acid derivative is an amino acid derivative of formula (A-1) or (A-2).

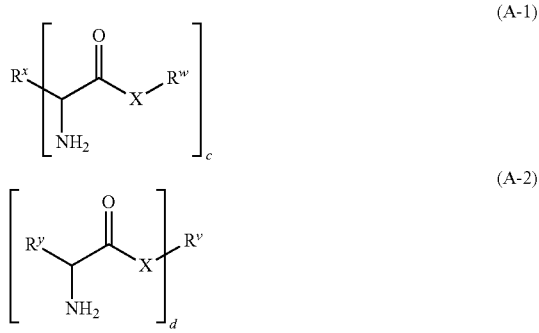

In the formulae, $R^x$ represents an aliphatic group or an aromatic group, $R^w$, $R^y$, and $R^v$ each independently represent an aliphatic group, an aromatic group, or a hydrogen atom, X represents an oxygen atom or a secondary amino group (—NH—), c represents 2 or 3, and d represent an integer of 1 to 4.

[3] The production method of a carbamic acid ester according to [1] or [2], wherein the amino acid derivative is an amino acid ester, the production method further containing a production step of an inorganic acid salt of the amino acid ester by reacting an amino acid and a compound having an alcoholic hydroxy group in the presence of an inorganic acid.

[4] The production method of a carbamic acid ester according to any one of [1] to [3], wherein the basic compound is an organic amine.

[5] The production method of a carbamic acid ester according to any one of [1] to [4], wherein the carbonic acid ester contains 0.001 ppm by mass to 10% by mass of a metallic atom, relative to the total mass of the carbonic acid ester.

[6] The production method of a carbamic acid ester according to any one of [1] to [5], wherein the inorganic acid salt of the amino acid derivative is supplied to the carbamation reactor in a liquid state.

[7] An isocyanate production method including: a thermal decomposition step in which a carbamic acid ester prepared by a production method of the carbamic acid ester of any one of [1] to [6] is subjected to a thermal decomposition reaction to obtain an isocyanate.

[8] The isocyanate production method according to [7], wherein the thermal decomposition step is conducted in a thermal decomposition reactor, the isocyanate production method further containing a washing step in which, after the thermal decomposition step, the thermal decomposition reactor is washed with an acid.

[9] The isocyanate production method according to [7] or [8], wherein the thermal decomposition reaction is conducted in a liquid phase.

Effects of the Invention

According to the present invention, a production method of a carbamic acid ester, by which the carbamation reaction efficiency and the separation and collection efficiency are improved, and an isocyanate production method in which the carbamic acid ester is used are provided.

EMBODIMENTS FOR CARRYING OUT THE INVENTION

Figure 1:
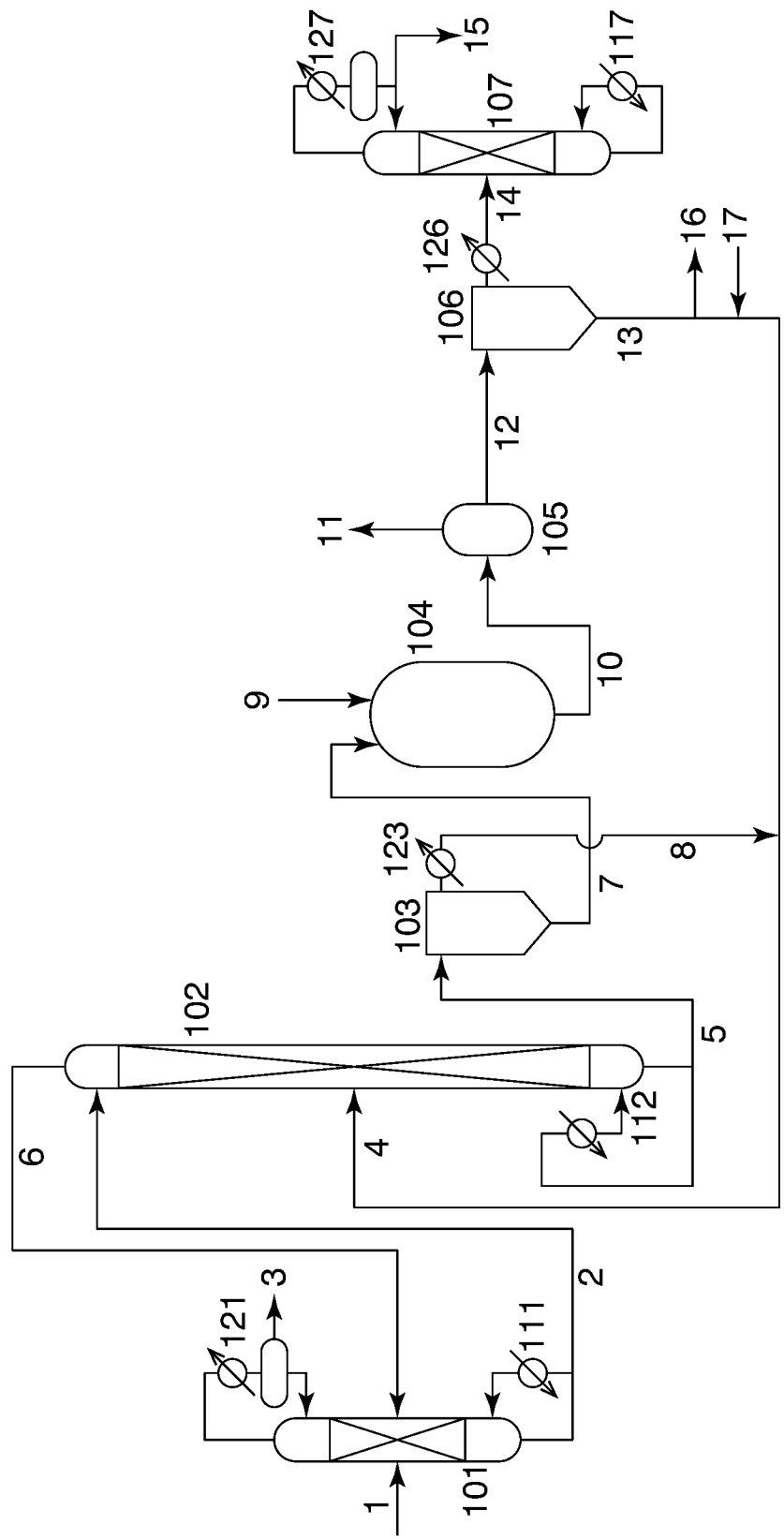
FIG. 1 indicates continuous production equipment used in Step (I-2) in Reference Example 1.

Embodiments for carrying out the present invention (hereinafter, referred to as "present embodiment") will be specifically described below. The below-mentioned present embodiments are examples to explain the present invention, and are not intended to limit the present invention to the below-mentioned present embodiments. The present invention may be modified in various ways within the summary thereof.

<Production Method of a Carbamic Acid Ester>

A production method of a carbamic acid ester according to the present embodiment contains: a carbamation step in which a carbonic acid ester, an inorganic acid salt of an amino acid derivative, and a basic compound are supplied to a carbamation reactor to allow the reaction to proceed to obtain a carbamic acid ester derived from the carbonic acid ester.

<<Carbamation Step>>

The carbamation step according to the present embodiment is a step in which a carbonic acid ester, an inorganic acid salt of an amino acid derivative and a basic compound are supplied to a carbamation reactor to allow the reaction to proceed to obtain a carbamic acid ester derived from the carbonic acid ester.

Although the conditions under which a carbonic acid ester, an inorganic acid salt of an amino acid derivative and a basic compound are reacted depend on compounds to be reacted, it is preferable that the stoichiometric proportion of the carbonic acid ester to an amino group of the inorganic acid salt of the amino acid derivative be 1 fold or more, and more preferably 1 fold to 1000 folds. In order to increase the reaction speed and terminate the reaction promptly, it is preferable that an excess amount of the carbonic acid ester, relative to an amino group of the inorganic acid salt of the amino acid derivative, be used, and the stoichiometric proportion thereof to an amino group of the inorganic acid salt of the amino acid derivative be 1.1 folds to 50 folds, and more preferably 1.5 folds to 10 folds, from the viewpoint of the size of a carbamation reactor.

Although the amount of the basic compound to be used may be appropriately determined depending on the compounds to be used, it is preferable that the stoichiometric proportion of the basic compound to be used, relative to an amino group of the inorganic acid salt of the amino acid derivative, be 0.001 folds or more, and more preferably 0.01 folds to 100 folds. Although it is not exactly clear the way in which the basic compound acts on the reaction in the carbamation step, it is assumed that the basic compound neutralizes an inorganic acid forming the inorganic acid salt of the amino acid derivative to increase the reactivity of an amino group of the amino acid derivative, and therefore it is preferable that the basic compound be used in an amount sufficient to neutralize the inorganic acid forming the inorganic acid salt of the amino acid ester. In order to allow neutralization to proceed promptly, a large amount of the basic compound is preferably used. However, from the viewpoint of suppressing activation of an ester group of the amino acid ester to suppress causing the side reaction, for example, it is preferable that the amount of the basic compound to be used, relative to the stoichiometric amount required to neutralize the inorganic acid, be 1 fold to 50 folds, more preferably 1.05 folds to 10 folds, and even more preferably 1.2 folds to 5 folds.

It is preferable that the carbonic acid ester, the inorganic acid salt of the amino acid derivative and the basic compound be reacted using an appropriate solvent in a liquid phase. Although the solvent may be appropriately selected depending on compounds to be used, examples thereof include aliphatic hydrocarbons, aromatic hydrocarbons, aromatic hydroxy compounds, alcohols, oxygen atom-containing compounds such as ethers, sulfur atom-containing compounds such as thiols and sulfides, halogenated aliphatic hydrocarbons, halogenated aromatic hydrocarbons, and water, and these compounds may be appropriately mixed to be used.

It is preferable that the inorganic acid salt of the amino acid derivative be supplied to the carbamation reactor in a liquid state. At the time, the inorganic acid salt of the amino acid derivative is preferably supplied in a state in which the inorganic acid salt is dissolved in a solvent, and the above-mentioned solvent is preferably used at the time. It is also preferable that the inorganic acid salt of the amino acid derivative be mixed with an alcohol, water, or a carbonic acid ester, to be supplied.

The reaction in the carbamation step is conducted by supplying the carbonic acid ester, the inorganic acid salt of the amino acid derivative and the basic compound into the carbamation reactor.

It is generally preferable that the reaction temperature be 0° C. to 150° C. Although a high temperature is preferable in order to increase the reaction speed, the reaction temperature is more preferably 10° C. to 100° C. from the viewpoint of suppression of unfavorable reaction. The carbamation reactor may be equipped with conventionally known cooling equipment or heating equipment to even out the reaction temperature.

Although the reaction pressure depends on the kinds of compounds to be used or the reaction temperature, any of reduced pressure, ordinary pressure, and increased pressure may be adopted, and the reaction pressure is generally 20 Pa to $1 \times 10^6$ Pa.

The reaction time (retention time in the case of a continuous method) is not particularly limited, and it is preferable that the reaction time be generally 0.001 hours to 50 hours, more preferably 0.01 hours to 20 hours, and even more preferably 0.1 hours to 10 hours. In addition, the reaction may be terminated after the reaction liquid is collected and then the production of the predetermined amount of the carbamic acid ester is confirmed by liquid chromatography, for example.

In the present embodiment, a catalyst may be used or may not be used in the reaction of the carbonic acid ester, the inorganic acid salt of the amino acid derivative and the basic compound, in addition to the compounds. In the case where no catalyst is used, thermal denaturation of the carbamic acid ester caused by the influence of metal components derived from the catalyst can be prevented.

In the case where a catalyst is used, the reaction can be terminated in a short time, and the reaction temperature can be lowered.

In the case where a catalyst is used, a basic catalyst, such as an organic compound or an inorganic compound of metal such as tin, lead, copper, or titanium, or an alcoholate of alkali metal or alkaline-earth metal, such as methylate, ethylate, or butylate (each isomer) of lithium, sodium, potassium, calcium, or barium, may be used.

A conventionally known tank-type reactor, tower-type reactor, or distillation column may be used as the carbamation reactor to be used to react the carbonic acid ester, the inorganic acid salt of the amino acid derivative and the basic compound. Although the reactor or lines may be formed by any of conventionally known materials, unless the materials exert harmful effects on starting substances or reaction substances, SUS 304, SUS 316, or SUS 316L is preferably used because of the low prices thereof (Carbamic Acid Ester)

In the step, a reaction mixture containing the carbamic acid ester derived from the carbonic acid ester (preferably a diaryl carbonate), the redundant carbonic acid ester, and a hydroxy compound derived from the carbonic acid ester (preferably an aromatic hydroxy compound) is obtained.

The carbamic acid ester obtained in the step is preferably a carbamic acid ester of formula (C).

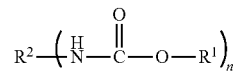

(C)

In the formula, $R^2$ represents a group derived from the inorganic acid salt of the amino acid derivative, $R^1$ represents a group derived from the carbonic acid ester, and n is an integer of 1 or more, and is the same number as that of amino groups of the inorganic acid salt of the amino acid derivative.

In the formula (C), n is preferably an integer of 1 to 4, more preferably an integer of 2 to 3, and even more preferably 3.

<Isocyanate Production Method>

In an isocyanate production method according to the present embodiment, the carbamic acid ester prepared from the carbonic acid ester by the above-mentioned production method of the carbamic acid ester is subjected to a thermal decomposition reaction to obtain an isocyanate. The isocyanate production method according to the present embodiment may encompass several aspects.

The isocyanate production method according to the present embodiment includes a thermal decomposition step in which, after the above-mentioned carbamation step, the resultant carbamic acid ester is subjected to a thermal decomposition reaction to obtain an isocyanate.

[Thermal Decomposition Step]

The thermal decomposition step is a step in which the above-mentioned carbamic acid ester is subjected to a thermal decomposition reaction to obtain an isocyanate.

The thermal decomposition reaction according to the present embodiment is a reaction in which an isocyanate and a hydroxy compound (preferably an aromatic hydroxy compound) are produced from the carbamic acid ester. The present step is preferably conducted in a liquid phase.

The reaction temperature is generally 100° C. to 300° C. Although a high temperature is preferable in order to increase the reaction speed, the reaction temperature is more preferably 150° C. to 250° C. from the viewpoint of suppression of side reaction. The thermal decomposition reactor may be equipped with conventionally known cooling equipment or heating equipment to even out the reaction temperature.

Although the reaction pressure depends on the kinds of compounds to be used or the reaction temperature, any of reduced pressure, ordinary pressure, and increased pressure may be adopted, and the reaction pressure is generally 20 Pa to $1 \times 10^6$ Pa.

Although the reaction time (retention time in the case of a continuous method) is not particularly limited, it is preferable that the reaction time be generally 0.001 hours to 100 hours, more preferably 0.005 hours to 50 hours, and even more preferably 0.01 hours to 10 hours.

Although the form of the thermal decomposition reactor is not particularly limited, conventionally known distillation equipment is preferably used to collect a gas phase component efficiently, and the thermal decomposition reactor is preferably composed of at least one reactor selected from the group consisting of an evaporator, a continuous multistage distillation column, a packed tower, a thin-film evaporator and a falling-film evaporator.

In addition, various conventionally known methods, such as a method in which a reactor containing any of a distillation column, a multistage distillation column, a multitubular reactor, a reactor internally equipped with a support, a forced circulation reactor, a falling-film evaporator, and a falling-drop evaporator is used, or a method in which these are combined may be adopted.

From the viewpoint of removing a low-boiling-point component (the hydroxy compound produced by the thermal decomposition reaction of the carbamic acid ester (preferably an aromatic hydroxy compound) and/or isocyanate) promptly from the reaction system, a tubular reactor is preferably used, a reactor such as a tubular thin-film evaporator or a tubular falling-film evaporator is more preferably used, and a structure having a large gas-liquid contact area that realizes prompt transfer of the resultant low-boiling-point component to the gas phase is preferable.

The kind of the carbamation reactor and the kind of the thermal decomposition reactor may be identical to or different from each other, and it is preferable that the carbamation reactor and the thermal decomposition reactor be at least one reactor selected from the group consisting of tower-type reactors and tank-type reactors.

In the thermal decomposition reactor, a thermal decomposition solvent may be present so as to ensure the wettability of the surface of the reactor and prevent adhesion of side reaction products.

The thermal decomposition solvent is preferably a compound having a boiling point higher than those of a hydroxy compound and an isocyanate prepared by the thermal decomposition of the carbamic acid ester, and examples thereof include: hydrocarbon compounds; polyethers such as polyethylene glycol alkyl ether; ester compounds such as phthalic acid derivatives, adipic acid derivatives, and trimellitic acid derivatives; polyisocyanates obtained by polymerizing diisocyanates such as hexamethylene diisocyanate, tolylene diisocyanate, or diphenylmethane diisocyanate; carbodiimides obtained by polymerizing diisocyanates such as hexamethylene diisocyanate, tolylene diisocyanate, or diphenylmethane diisocyanate; sulfur-containing compounds such as sulfones and sulfides; ionic liquids; alcohols; silicon-containing compounds such as alkyl silicone compounds, cyclic or linear polysiloxanes; tertiary amines; ketones; hetero-ring- and/or condensed-ring-containing compounds, polyimides, phosphate esters; and aromatic hydroxy compounds. Among these, phenol is preferably used.

Although the thermal decomposition reactor may be formed by any of conventionally known materials, unless the materials exert harmful effects on the carbamic acid ester or the resultant hydroxy compound or isocyanate, SUS 304, SUS 316, or SUS 316L is preferably used because of the low prices thereof.

[Transfer Step]

It is preferable that a transfer step be conducted between the carbamation step and the thermal decomposition step.

In the transfer step, the reaction mixture containing the carbamic acid ester prepared in the carbamation step is transferred to the thermal decomposition reactor connected with the carbamation reactor via a pipe arrangement (line).

The present embodiment makes it possible to increase the yields of each reactions by separating the carbamation reactor and the thermal decomposition reactor to select each reactor suitable for each reactions, and thereby allowing each of the reaction conditions to be set flexibly.

The carbamic acid ester often has a high boiling point, because a hydrogen bond is easily formed between molecules thereof due to a urethane bond forming the carbamic acid ester. When such a carbamic acid ester is transferred, a solid carbamic acid ester may be subjected to a shaping treatment such as pulverization or pelletization, for example.

However, the transfer of the solid carbamic acid ester subjected to the shaping treatment often causes obstruction of transfer lines, requires cumbersome equipment to stably transfer a constant amount of the carbamic acid ester having variation in the form thereof, or requires a step for uniforming the shape of the carbamic acid ester in a range. Thus, the carbamic acid ester is preferably transferred in a liquid state to be supplied to the thermal decomposition reactor.

In the method for transferring a carbamic acid ester in a liquid state to a thermal decomposition reactor to conduct supplying, the reaction mixture is preferably supplied to the thermal decomposition reactor in a liquid state. The reaction mixture obtained in the carbamation step may be directly transferred to be supplied. Alternatively, in the case where a carbamic acid ester is purified from the reaction mixture obtained by the carbamation step, the reaction mixture may be transferred to be supplied as a liquid mixed with the thermal decomposition solvent.

The reaction mixture obtained by the carbamation step is often in a uniform liquid state at a temperature lower than the melting point of the carbamic acid ester even when the reaction mixture is liquid or solid at normal temperature (20° C.), and therefore heating is not required to prevent solidification and the thermal denaturation reaction of the carbamic acid ester can be suppressed.

The reaction mixture is preferably transferred at a temperature of 10° C. to 180° C., more preferably 30° C. to 170° C., and even more preferably 50° C. to 150° C.

The method for supplying a carbamic acid ester to the thermal decomposition reaction as the reaction mixture obtained by reacting a carbonic acid ester and an inorganic acid salt of an amino acid derivative has an advantage in that the step can be simplified, because the reaction mixture is supplied continuously without conducting distillation and separation processes and the like.

In addition, in the method for supplying a mixture obtained by separating a part of or all of hydroxyl compounds (for example, aromatic hydroxy compounds) from the reaction mixture, a step for isolating only a carbamic acid ester from the reaction mixture is not required, and therefore the step can be simplified.

Although the lines may be formed by any of conventionally known materials, unless the materials exert harmful effects on the carbamic acid ester or the resultant hydroxy compound or isocyanate, SUS 304, SUS 316, or SUS 316L is preferably used because of the low prices thereof.

[Washing Step]

It is preferable that a washing step be conducted after the thermal decomposition step.

There is a case where polymeric by-products derived from the side reaction of formula (8), (9), or (10), for example, are generated accompanying the thermal decomposition reaction of a carbamic acid ester, and then the by-products generated by the thermal decomposition reaction are also adhered to the thermal decomposition reactor.

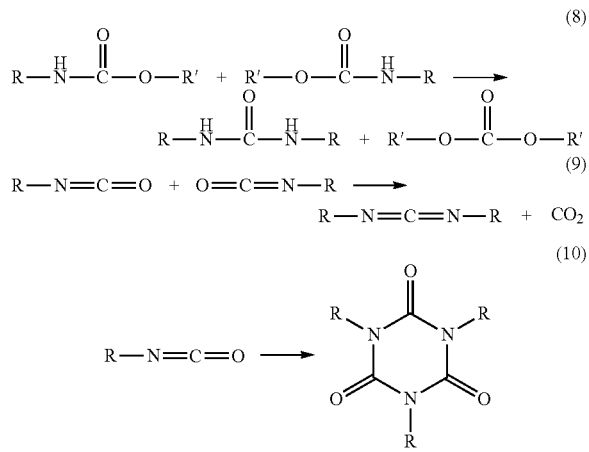

In the formulae (8) to (10), R represents a group derived from a carbamic acid ester.

The polymeric by-products adhered to the thermal decomposition reactor are compounds formed singularly by a bond represented by the first member of the right side of formula (8), the first member of the right side of formula (9), or the right side of formula (10) or formed by combining at least two bonds thereof. The inside of the thermal decomposition reactor (particularly the wall surface) can be maintained cleanly by washing the wall surface of the thermal decomposition reactor with an acid, and dissolving the polymeric by-products therewith to remove the polymeric by-products from the thermal decomposition reactor. Such a method makes it possible to wash the wall surface of the thermal decomposition reactor without dismantling the thermal decomposition reactor to conduct washing separately, and significantly shortens the non-operation period of the thermal decomposition reactor, and thereby further improving the production efficiency of an isocyanate.

As a method for washing the thermal decomposition reactor using the acid (washing solvent), various methods, such as a method in which the thermal decomposition reactor is washed by introducing the washing solvent from an upper portion of the thermal decomposition reactor, or a method in which the inside of the thermal decomposition reactor is washed by introducing the washing solvent into the bottom of the thermal decomposition reactor, and then the washing solvent is boiled in the thermal decomposition reactor, may be adopted.

The washing process is not required to be conducted at every step in which the thermal decomposition reaction is conducted, and may be arbitrarily conducted depending on used compounds, operation rate, or the like. The washing process is preferably conducted once per 1 hour to 20000 hours of operating time, more preferably once per 1 day to 1 year of operating time, and particularly preferably once per 1 month to 1 year of operating time. The thermal decomposition reactor may be equipped with a line configured to introduce the washing solvent.

The washing solvent may be made to coexist under the conditions of the thermal decomposition reaction to wash the thermal decomposition reactor, when the thermal decomposition reaction of a carbamic acid ester is conducted. The washing solvent is different from inactive solvents conventionally used in the prior art (see, for example, U.S. Pat. No. 4,081,472), and can react with an isocyanate produced by thermal decomposition of a carbamic acid ester. The washing solvent may be mixed with the reaction mixture obtained by the carbamation step at the step of transferring to the thermal decomposition reactor to supply the resultant to the thermal decomposition reactor, or may be supplied via a line configured to supply the washing solvent, the line being provided separately from a line configured to supply the reaction mixture.

[Collecting Step 1]

A collecting step 1 is preferably conducted after the thermal decomposition step and/or at the same time as the thermal decomposition step.

The step is a step in which a low-boiling-point component produced by the thermal decomposition step is collected from the thermal decomposition reactor as a gas phase component and a liquid phase component is collected from the bottom of the thermal decomposition reactor.

It is preferable that the time in which the carbamic acid ester and the isocyanate produced by thermal decomposition reaction are maintained at a high temperature be shortened as much as possible, so as to prevent side reaction, and the thermal decomposition reaction be conducted by a continuous method.

The continuous method is a method in which a mixture containing the carbamic acid ester is continuously supplied to the thermal decomposition reactor to allow the thermal decomposition reaction to proceed, and then the resultant isocyanate and the resultant hydroxy compound (preferably aromatic hydroxy compound) are continuously removed from the thermal decomposition reactor. It is preferable that, in the continuous method, a low-boiling-point component produced by the thermal decomposition reaction of the carbamic acid ester (the resultant isocyanate and the resultant hydroxy compound) be collected from the upper portion of the thermal decomposition reactor as a gas phase component, and the remaining component be collected from the bottom of the thermal decomposition reactor as a liquid phase component. It is preferable that the collection step of the gas phase component and the collection step of the liquid phase component be conducted continuously.

Although all compounds present in the thermal decomposition reactor may be collected as gas phase components, the presence of a liquid phase component in the thermal decomposition reactor allows polymeric by-products produced by side reaction caused by the carbamic acid ester and/or the isocyanate to be dissolved therein, and thereby exhibiting effects of preventing adhesion and accumulation of the polymeric by-products to the thermal decomposition reactor. Although the thermal decomposition reaction of the carbamic acid ester produces an isocyanate and an (aromatic) hydroxy compound, at least one compound of these compounds is collected as a gas phase component. The target compound to be collected as a gas phase component depends on conditions of the thermal decomposition reaction. As mentioned above, it is preferable that a thermal decomposition solvent be made to coexist as a liquid phase component.

The term "low-boiling-point component produced by thermal decomposition reaction of the carbamic acid ester" used in the present embodiment refers to an (aromatic) hydroxy compound and/or an isocyanate produced by thermal decomposition reaction of the carbamic acid ester, and the team particularly refers to a compound which can exist in a gas state under conditions under which the thermal decomposition reaction is conducted.

[Collecting Step 2]

It is preferable that a collecting step 2 be conducted after the thermal decomposition step and/or at the same time as the thermal decomposition step.

For example, in the case where a reaction liquid obtained by conducting the carbamation step is directly used to allow the redundant carbonic acid ester to coexist in the reaction liquid, a method in which an isocyanate and a hydroxy compound (preferably an aromatic hydroxy compound), produced by the thermal decomposition reaction, and the carbonic acid ester are collected as gas phase components, and a liquid phase component containing the carbamic acid ester is collected from the bottom of the thermal decomposition reactor may be adopted. Also in the method, it is preferable that the gas components containing the collected isocyanate be supplied in a gas state to distillation equipment configured to produce and separate the isocyanate.

In addition, a method in which an isocyanate and a hydroxy compound (preferably an aromatic hydroxy compound) produced by decomposition reaction is collected as gas phase components, and liquid phase components containing a carbonic acid ester and/or a carbamic acid ester are collected may also be adopted, for example. In the method, the isocyanate and the hydroxy compound (preferably the aromatic hydroxy compound) may be collected separately in the thermal decomposition reactor. It is preferable that the gas phase components containing the collected isocyanate be supplied in a gas phase to distillation equipment configured to purify and separate the isocyanate.

On the other hand, the liquid phase components containing the carbonic acid ester and/or the carbamic acid ester are separated and collected from the bottom of the thermal decomposition reactor. In the case where the liquid phase components contain the carbonic acid ester, it is preferable that the carbonic acid ester be separated and collected from the liquid phase components to reuse the carbonic acid ester. In the case where the liquid phase components contain the carbamic acid ester, it is preferable that a part or all of the liquid phase components be supplied to the top portion of the thermal decomposition reactor to subject the carbamic acid ester to the thermal decomposition reaction again. The upper portion of the thermal decomposition reactor refers to the second stage or higher stage from the column bottom as the theoretical stage number in the case where the thermal decomposition reactor is a distillation column, and refers to the portion upper than a heat transfer area which is heated in the case where the thermal decomposition reactor is thin-film distillation equipment. In the case where a part or all of the liquid phase components are supplied to the upper portion of the thermal decomposition reactor, it is preferable that the liquid phase components be maintained at 50° C. to 180° C., more preferably 70° C. to 170° C., and even more preferably 100° C. to 150° C. to be transferred.

In addition, a method in which, from an isocyanate and a hydroxy compound (aromatic hydroxy compound) produced by thermal decomposition reaction, the hydroxy compound (aromatic hydroxy compound) is collected as a gas phase component and a mixture containing the isocyanate is collected as a liquid phase component from the bottom of the thermal decomposition reactor may be adopted, for example. In this case, the liquid phase component is supplied to distillation equipment to collect the isocyanate. In the case where the carbonic acid ester be contained in the liquid phase component, the carbonic acid ester is preferably separated and collected to be reused. In the case where the a carbamic acid ester be contained in the liquid phase component, it is preferable that a part or all of the mixture containing the carbamic acid ester be supplied to the upper portion of the thermal decomposition reactor to subject the carbamic acid ester to a thermal decomposition reaction again.

In the case where a part or all of the liquid phase components is supplied to the upper portion of the thermal decomposition reactor, the liquid phase component is preferably maintained at 50° C. to 180° C., more preferably 70° C. to 170° C., and even more preferably 100° C. to 150° C. to be transferred.

As mentioned above, in the thermal decomposition reaction, the liquid phase component is preferably collected from the bottom of the thermal decomposition reactor, because the presence of the liquid phase component in the thermal decomposition reactor makes it possible to dissolve polymeric by-products generated by side reaction induced by the carbamic acid ester and/or the isocyanate to exhaust the polymeric by-products as liquid phase components from the thermal decomposition reactor, and thereby exhibiting effects of reducing adhesion and accumulation of the polymeric compound to the thermal decomposition reactor.

In the case where the carbamic acid ester is contained in the liquid phase component, a part or all of the liquid phase component is supplied to the upper portion of the thermal decomposition reactor to subject the carbamic acid ester to a thermal decomposition reaction again, but repeated conducting of the step may cause accumulation of polymeric by-products in the liquid phase component. In this case, a part or all of the liquid phase component may be removed from the reaction system to reduce accumulation of polymeric by-products or maintain the amount of the polymeric by-products at a constant level.

The hydroxy compound (aromatic hydroxy compound) and/or carbonic acid ester contained in the gas phase component and/or the liquid phase component obtained in the thermal decomposition reaction are respectively separated and collected to be reused.

Specifically, the aromatic hydroxy compound may be reused as a reaction solvent in the carbamation step, and/or, an aromatic hydroxy compound to be used to prepare a carbonic acid ester, and the carbonic acid ester may be reused as a raw material to be used to prepare a carbamic acid ester.

<Materials>

Each of the materials to be used in the present embodiment will be explained below.

<<Carbonic Acid Ester>>

A carbonic acid ester available in the production method according to the present embodiment is preferably a compound of formula (1).

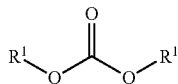
(1)

In the formula, $R^1$ each independently represents a C1-20 aliphatic hydrocarbon group, or, a C6-20 aromatic group.

In the case where $R^1$ represents a C1-20 aliphatic hydrocarbon group, the hydrocarbon group may be linear or branched.

Examples of an aliphatic hydrocarbon as $R^1$ include alkyl groups. The carbon number of the alkyl group is preferably 1 to 5, more preferably 1 to 4, and even more preferably 1 or 2. Specific examples thereof include a methyl group, an ethyl group, a n-propyl group, a n-butyl group, and a n-pentyl group. The carbon number of the branched alkyl group is preferably 3 to 10, and more preferably 3 to 5. Specific examples thereof include an isopropyl group, an isobutyl group, a tert-butyl group, an isopentyl group, a neopentyl group, a 1,1-diethylpropyl group, and a 2,2-dimethylbutyl group.

An alicyclic hydrocarbon group may be polycyclic or monocyclic. Examples of the monocyclic alicyclic hydrocarbon group include cyclopentane and cyclohexane. Examples of the polycyclic alicyclic hydrocarbon group include adamantane, norbornane, isobornane, tricyclodecane, and tetracyclododecane.

As $R^1$ in the formula (1), a C6-20 aromatic hydrocarbon group is preferable, and a C6-12 aromatic hydrocarbon group is more preferable. Although $R^1$ may be an aromatic hydrocarbon having a carbon number of 21 or more, the number of carbon constituting $R^1$ is preferably 20 or less, from the viewpoint of making it easy to conduct separation from an isocyanate produced by thermal decomposition reaction of the carbamic acid ester.

Examples of $R^1$ include a phenyl group, a methylphenyl group (each isomer), an ethylphenyl group (each isomer), a propylphenyl group (each isomer), a butylphenyl group (each isomer), a pentylphenyl group (each isomer), a hexylphenyl group (each isomer), a dimethylphenyl group (each isomer), a methylethylphenyl group (each isomer), a methylpropylphenyl group (each isomer), a methylbutylphenyl group (each isomer), a methylpentylphenyl group (each isomer), a diethylphenyl group (each isomer), an ethylpropylphenyl group (each isomer), an ethylbutylphenyl group (each isomer), a dipropylphenyl group (each isomer), a trimethylphenyl group (each isomer), a triethylphenyl group (each isomer), and a naphthyl group (each isomer).

Among these diaryl carbonates, diaryl carbonates in which $R^1$ represents a C6-8 aromatic hydrocarbon group are preferable, and examples of such diaryl carbonates include diphenyl carbonate, di(methylphenyl) carbonate (each isomer), di(diethylphenyl) carbonate (each isomer), and di(methylethylphenyl) carbonate (each isomer).

It is preferable according to the present embodiment that the compound of formula (1) be a diaryl carbonate of formula (1)-1.

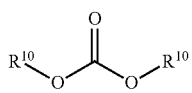
(1)-1

In the formula, $R^{10}$ each independently represents a C6-20 aromatic hydrocarbon group.

$R^{10}$ in the formula (1)-1 is a C6-20 aromatic hydrocarbon group, preferably a C6-12 aromatic hydrocarbon group, more preferably a C6-8 aromatic hydrocarbon group, and even more preferably a phenyl group.

It is preferable that the carbonic acid ester or the diaryl carbonate contain a metallic atom in an amount of 0.001 ppm by mass to 10% by mass, more preferably 0.001 ppm by mass to 5% by mass, and particularly preferably 0.002 ppm by mass to 3% by mass, relative to the total mass of the carbonic acid ester or the diaryl carbonate.

The metallic atom may be present as a metallic ion or a single body of a metallic atom. As the metallic atom, a divalent to tetravalent metallic atom is preferable, and, among these, one kind or plural kinds of metal selected from the group consisting of iron, cobalt, nickel, zinc, tin, copper, and titanium is (are) preferable.

As the production method of the carbonic acid ester or the diaryl carbonate, a conventionally known method may be adopted. As an example thereof, a method, disclosed by WO 2009/139061, in which an organic tin compound having a tin-oxide-carbon bond and carbon dioxide are reacted to produce a carbonic acid ester, and then a diaryl carbonate is produced from the carbonic acid ester and an aromatic hydroxy compound, is preferably adopted. The carbonic acid ester or the diaryl carbonate is purified by a conventionally known method such as distillation, and is preferably used as the carbonic acid ester or the diaryl carbonate according to the present embodiment. The above-mentioned metallic atom may be contained in the carbonic acid ester or the diaryl carbonate within the above-mentioned preferable range depending on the production method of the carbonic acid ester or the diaryl carbonate, production conditions, purification methods or purification conditions, and, in such a case, the carbonic acid ester or the diaryl carbonate may be directly used. In the case where the amount of the metallic atom contained in the carbonic acid ester or the diaryl carbonate is lower than the above-mentioned range, a metallic atom may be added separately as an organic acid salt such as an acetic acid salt or naphthenic acid salt, a chloride, or an acetylacetone complex, for example. In the case where the amount is higher than the above-mentioned range, the amount of the metallic atom may be decreased for use to the above-mentioned range by conducting solvent-washing, distillation-purification, crystallization, removal using an ion-exchange resin, or removal using a chelate resin. The amount of the metallic component contained in the carbonic acid ester or the diaryl carbonate may be determined by a conventionally known method, and the method may be selected from various methods such as an atomic absorption analysis method, an inductively coupled plasma emission spectrometry method, an inductively coupled plasma mass spectrometry method, an x-ray fluorescence spectrometry method, x-ray photoelectron spectrometry method, electron probe micro analyzer, or secondary ion mass spectrometry method, in view of the sample form, or the amount of the contained metallic component.

The metallic atom may be present as a metallic ion or a single body of a metallic atom. As the metallic atom, a divalent to tetravalent metallic atom is preferable, and, among these, one kind or plural kinds of metal selected from the group consisting of iron, cobalt, nickel, zinc, tin, copper, and titanium is (are) preferable, and iron is more preferable.

The present inventors surprisingly found that the use of the diaryl carbonate containing the metallic atom in an amount of the above-mentioned range exhibits effects of suppressing the degeneration reaction of the carbamic acid ester produced in the reaction of the diaryl carbonate and an inorganic acid salt of an amino acid derivative. Although the mechanism by which such effects are exhibited is not clear, the present inventors assume that the metallic atom coordinates to a urethane bond (—NHCOO—) of the carbamic acid ester produced in the reaction, and thereby stabilizing the urethane bond to suppress the side reaction. Although the effects of suppressing the degeneration reaction of the carbamic acid ester by the metallic atom are also confirmed in the transfer step of the reaction liquid containing a carbamic acid ester mentioned below, it is assumed that the mechanism is the same as mentioned above.

Although it is expected that similar effects are exhibited by mixing a carbonic acid ester and an inorganic acid salt of an amino acid derivative to produce a mixture, followed by adding a metallic atom exemplified above to the mixture in an amount of the above-mentioned range, it was revealed from the intensive study by the present inventors that the above-mentioned effects are hardly exhibited only by adding a metallic atom to the mixture of a carbonic acid ester and an inorganic acid salt of an amino acid derivative. Although the reason causing such a result is not clear, the present inventors assumed that the diaryl carbonate coordinates to a metallic atom contained in the diaryl carbonate, while the metallic atom added to the mixture of the diaryl carbonate and the inorganic acid salt of the amino acid derivative strongly coordinates to the inorganic acid salt of an amino acid derivative and thereby the produced carbamic acid ester hardly coordinates to a urethane bond, because the interaction of the metallic atom and the inorganic acid salt of the amino acid derivative is larger than the interaction of the metallic atom and the diaryl carbonate.

There are few cases where the catalytic action exhibited by the metallic atom contained in the carbonic acid ester in an amount of the above-mentioned range in the reaction of the carbonic acid ester and the inorganic acid salt of the amino acid ester is confirmed, and in the sense the metallic atom is clearly distinguished from the catalyst to be used to prepare the carbamic acid ester.

<<Inorganic Acid Salt of the Amino Acid Derivative>>

The term "amino acid derivative" used in the present embodiment refers to a compound synthesized using an amino acid as a raw material. The amino acid may be a natural amino acid or a synthesized amino acid, as mentioned below.

The inorganic acid salt of the amino acid derivative available in the present embodiment is preferably an inorganic acid salt of an amino acid derivative of the below-shown formula (A-1) or (A-2).

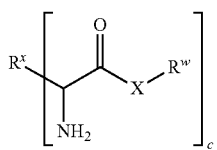
(A-1)

In the formula, $R^x$ represents an aliphatic group or an aromatic group.

X represents an oxygen atom, or a secondary amino group (—NH—), and preferably represents an oxygen atom.

$R^w$ represents a C1-15 aliphatic group, a C6-15 aromatic group, or a hydrogen atom, and c preferably represents 2 or 3.

In the formula (A-1), $R^x$ preferably represents an aliphatic group having a carbon number of 1 or more or an aromatic group having a carbon number of 6 or more, which may have a primary amino group, a sulfur atom, an oxygen atom, or a halogen atom, more preferably has a structure formed by removing —NHCOOH group from an amino acid, and even more preferably a C1-15 aliphatic group or a C6-15 aromatic group.

α-amino acids have two possible sterically binding modes of an amino group or a carboxyl group to an a carbon, and are respectively distinguished as D-type or L-type photoisomer. The amino acid (and a compound having an amino acid skeleton) available in the present embodiment may be D-type, L-type, a mixture thereof, or a racemic body. Many industrially inexpensively available amino acids are amino acids produced by fermentation, and are almost all L-type, which are preferable. Although the steric configuration is not shown in the present specification, the steric configuration is either D-type or L-type.

Specific examples of the compound of formula (A-1) include compounds of the following formulae.

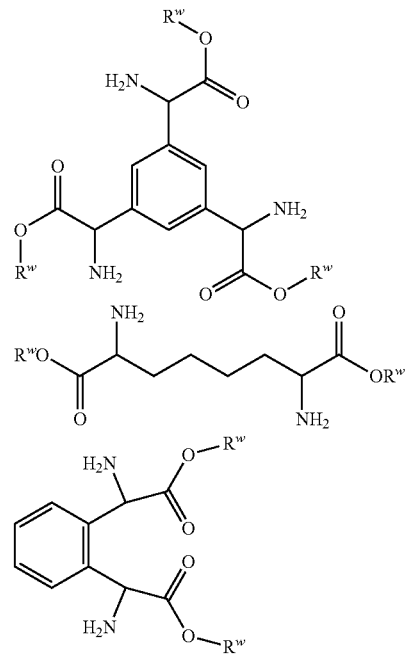

In the formulae, $R^w$ is as described above, preferably a C1-6 alkyl group, and more preferably a C1-3 alkyl group.

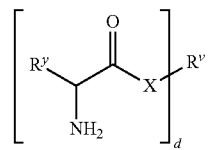
(A-2)

In the formula, $R^y$ represents an aliphatic group, an aromatic group or a hydrogen atom.

X represents an oxygen atom or a secondary amino group (—NH—), and preferably represents an oxygen atom.

$R^v$ represents a C1-15 aliphatic group, a C6-15 aromatic group, or a hydrogen atom, and d represents an integer of 1 to 4.

In the formula (A-2), $R^y$ preferably represents an aliphatic group having a carbon number of 1 or more or an aromatic group having a carbon number of 6 or more, which may contain a primary amino group, a sulfur atom, an oxygen atom, or a halogen atom, or a halogen atom, more preferably a C1-15 aliphatic group which may contain a group selected from the group consisting of groups of the below-shown formulae (i) to (iv), a C6-15 aromatic group which may contain a group selected from the group consisting of groups of the formulae (i) to (iv), a C7-17 group in which an aliphatic group and an aromatic group are bonded, and which may contain a group selected from the group consisting of groups (i) to (iv), a group of formula (I) or (II) shown below, or a hydrogen atom.

—O— (i)

—S— (ii)

NH$_2$— (iii)

—S—S— (iv)

In the formulae (i) to (iv), an atom to which a nitrogen atom or a sulfur atom is bonded is a carbon atom.

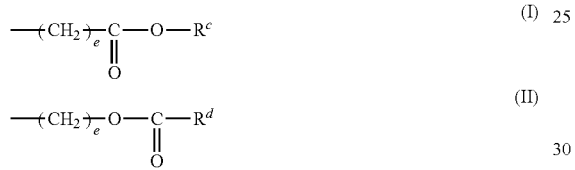

(I)

(II)

In the formula (I), $R^c$ represents a group of the below-shown formula (III), (IV), or (V), or a C1-10 hydrocarbon group, and e represents an integer of 0 to 5. In the formula (II), $R^d$ represents a C1-15 aliphatic hydrocarbon group or a C6-15 aromatic hydrocarbon group, and e represents an integer of 0 to 5.

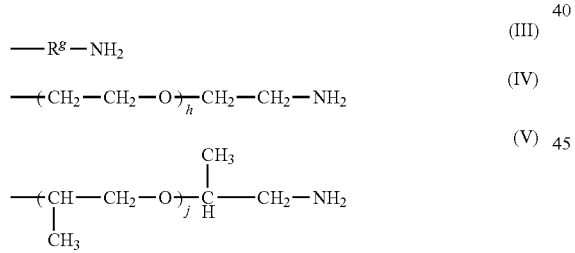

(III)

(IV)

(V)

In the formulae, $R^g$ represents a C1-10 aliphatic hydrocarbon group (preferably a C1-6 linear or branched alkylene group), h represents an integer of 1 to 9, and j represents an integer of 0 to 9.

In the present embodiment, an amino acid ester is preferable as an amino acid derivative. Accordingly, preferable examples of the compound of formula (A-2) include compounds of formulae (A-3) to (A-6).

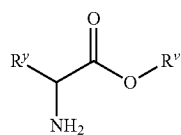

(A-3)

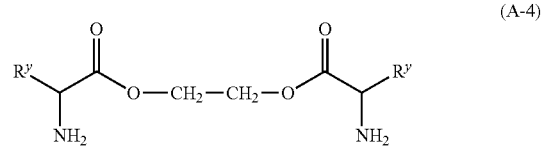

(A-4)

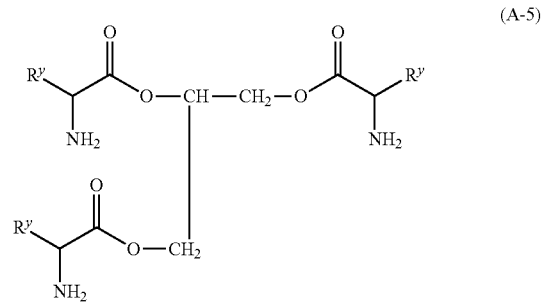

(A-5)

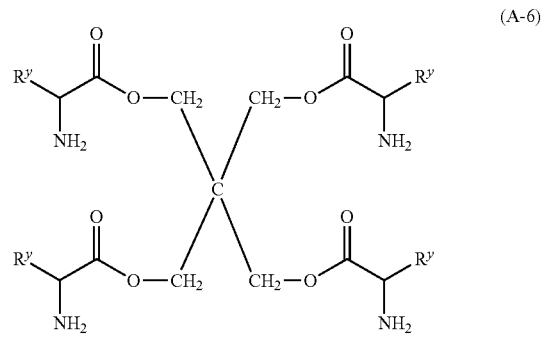

(A-6)

In the present embodiment, an amino acid ester of formula (11) shown below is also preferably used as an amino acid ester of an inorganic acid salt.

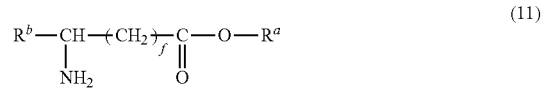

(11)

In the formula (11), f represents 1 or 2.

$R^a$ is a C1-15 aliphatic group which may contain a group of formula (i) or (ii) shown below, a C6-15 aromatic group which may contain a group of formula (i) or (ii) shown below, a C7-15 group in which an aliphatic group and an aromatic group are bonded, and which may contain a group of formula (i) or (ii) shown below, or a group of formula (III), (IV), or (V) shown below.

—O— (i)

—S— (ii)

In the formulae (i) and (ii), an atom with which an oxygen atom or a sulfur atom is bonded is a carbon atom.

(III)

(IV)

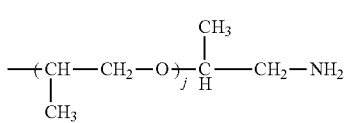
(V)

In the formulae, $R^g$ represents a C1-10 aliphatic hydrocarbon group (preferably a C1-6 linear or branched alkylene group), h represents an integer of 1 to 9, and j represents an integer of 0 to 9.

In the formula (11), $R^b$ represents a C1-15 aliphatic group which may have a group selected from groups of formulae (i) to (iv), a C6-15 aromatic group which may have a group selected from groups of formulae (i) to (iv), a C7-15 group in which an aliphatic group and an aromatic group are bonded and which may have a group selected from groups of formulae (i) to (iv), a group of formula (I) or (II), or a hydrogen atom.

It is more preferable that a salt formed from an amino acid ester of below shown formula and an inorganic acid be used.

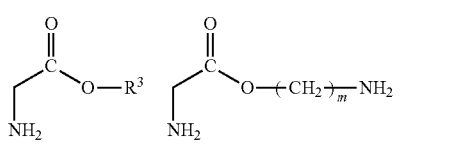

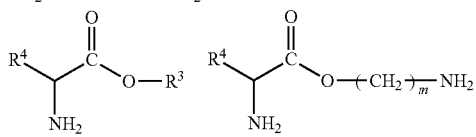

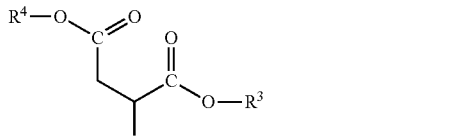

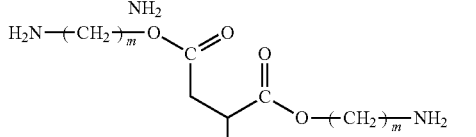

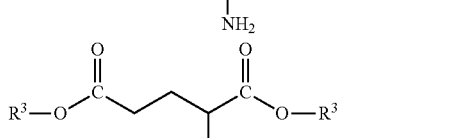

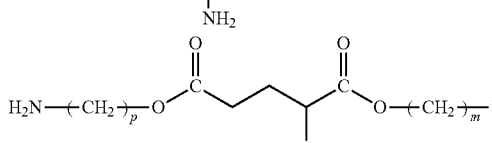

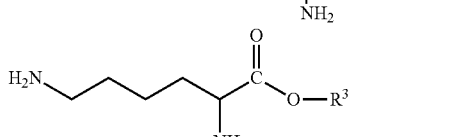

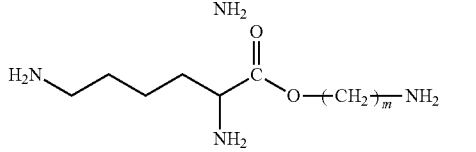

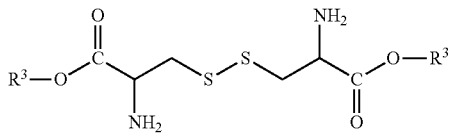

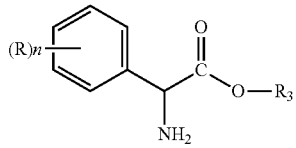

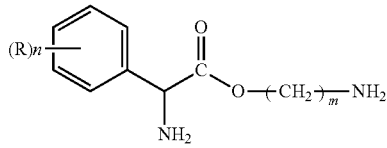

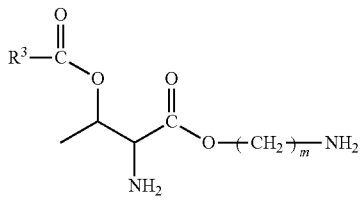

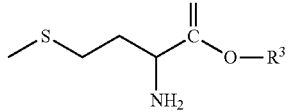

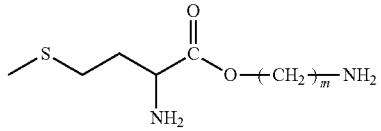

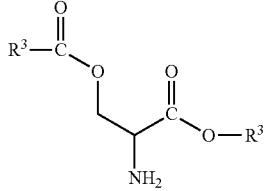

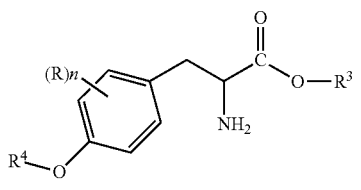

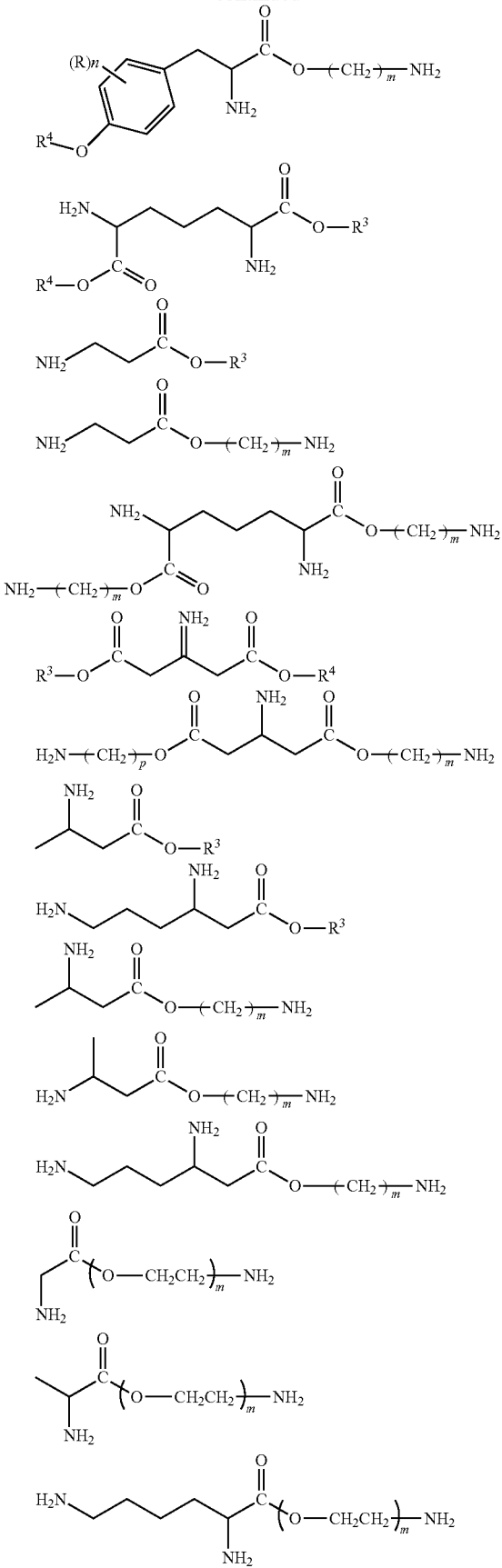

In the formulae, $R^3$ and $R^4$ each independently represent a C1-10 aliphatic hydrocarbon group or a hydrogen atom, R represents a halogen atom, a C1-6 alkyl group, or a C1-6 alkoxy group, n represent an integer of 0 to 2, and m and p each independently represent an integer of 1 to 10 (preferably 1 to 6, and more preferably 1 to 3).

Among these, compounds of the below-shown formulae are preferable.

In the formulae, $R^3$, $R^4$, R, n and m are the same as defined above. Preferably, $R^3$ represents a C1-4 alkyl group, $R^4$ represents a C1-6 alkyl group, R represents a halogen atom, a C1-4 alkyl group, or a C1-4 alkoxy group, n represents 1 or 2, and m represents an integer of 1 to 6.

Among these, an amino acid ester derived from a lysine skeleton, such as lysine methyl ester, lysine ethyl ester, or lysine β-aminoethyl ester, an amino acid ester derived from a glutamic acid skeleton, such as glutamic acid methyl ester, or glutamic acid di(β-aminoethyl) ester, an amino acid ester derived from a methionine skeleton, such as methionine methyl ester, an amino acid ester derived from a glycine skeleton, such as glycine methyl ester, an amino acid ester derived from a phenylalanine skeleton, such as phenylalanine methyl ester, an amino acid ester derived from an asparaginic acid skeleton, such as asparaginic acid methyl ester, an amino acid ester derived from an alanine skeleton, such as alanine methyl ester, an amino acid ester derived from a leucine skeleton, such as leucine methyl ester, an amino acid ester derived from an isoleucine skeleton, such as isoleucine methyl ester, or an amino acid ester derived from a valine skeleton, such as valine methyl ester is particularly preferable.

For example, the amino acid ester preferably used in the present embodiment may be prepared by reacting an amino acid and a compound having an alcoholic hydroxy group in the presence of an inorganic acid, or, reacting an inorganic acid salt of an amino acid and an inorganic acid salt of an aminoalcohol in the presence of an inorganic acid.

Although an arbitrary inorganic acid such as hydrochloric acid, nitric acid, phosphoric acid, sulfuric acid, boric acid, or hydrofluoric acid may be used as the inorganic acid, sulfuric acid, phosphoric acid, or hydrochloric acid is preferably used, and hydrochloric acid is more preferably used.

An inorganic acid salt of the amino acid ester available in the present embodiment is formed with the above-mentioned inorganic acid, and is preferably a sulfuric acid salt of an amino acid ester, a phosphoric acid salt of an amino acid ester, or a hydrochloric acid salt of an amino acid ester, and is more preferably a hydrochloric acid salt of an amino acid ester.

An amino acid is preferably a C2-18 aliphatic or aromatic amino acid having at least one amino group and at least one carboxyl group, or a 3-membered to 12-membered lactam.

The amino acid may be a natural amino acid or a synthesized amino acid.

Examples of the natural amino acid include alanine, arginine, asparagine, glutamine, glutamic acid, glycine, histidine, isoleucine, leucine, lysine, asparaginic acid, methionine, phenylalanine, tryptophan, valine, and ornithine.

The synthesized amino acid may be produced by a conventionally known method, such as Strecker synthesis using an aldehyde compound. A compound of formula (B) shown below may be used as the aldehyde.

(B)

In the formula, $R^Z$ represents an aliphatic group having a carbon number of 1 or more or an aromatic group having a carbon number of 6 or more, which may include an oxygen atom or a halogen atom, and, and z represents an integer of 1 to 3.

In the formula, the carbon number of $R^Z$ is preferably 1 to 12, and specific preferable examples of the compound (B) include acetaldehyde, propionaldehyde, hexylaldehyde, octylaldehyde, caprinaldehyde, phenylacetaldehyde, benzaldehyde, dimethoxybenzaldehyde, chlorobenzaldehyde, fluorobenzaldehyde, heliotropine, cyclamenbenzaldehyde, furfural, naphthaldehyde, and phthaldehyde. In the case where the compound has an isomer structure, the isomer is also contained.

An inorganic acid salt of an amino acid is an inorganic acid salt of the above-mentioned amino acid.

Examples of the amino acid particularly preferably used include aliphatic monoamino monocarboxylic acids, diamino monocarboxylic acids, monoamino dicarboxylic acids, and diamino dicarboxylic acids. Lactams formed by cyclization of these amino acids are also preferably used. Specific examples of the compound include glycine, 3-aminoproprionic acid, ω-aminocaproic acid, co-aminolauric acid, alanine, isoleucine, 3-aminobutyric acid, 4-aminocyclohexanecarboxylic acid, phenylalanine, methionine, aminobenzoic acid, asparaginic acid, glutamic acid, lysine, lanthionine, 1-amino-2,3,4-butane tricarboxylic acid, lactams of the above-mentioned amino acids, pyrolidone, caprolactam, and laurolactam.

The compound having an alcoholic hydroxy group is preferably an inorganic acid salt of an aminoalcohol.

The inorganic acid salt of an aminoalcohol may be produced by reacting the inorganic acid salt of an amino acid and an alcohol.

The inorganic acid salt of an aminoalcohol is an inorganic acid salt of a C2-12 aminoalcohol having one primary or secondary hydroxyl group and one primary amino group. The aminoalcohol may contain, in an alkylene chain thereof, a hetero atom such as oxygen or sulfur, or a group inactive against esterification, such as a substituent such as nitro, halogen, alkyl, or phenyl group. Specific examples of the aminoalcohol include ethanolamine, 1-amino2-propanol, 2-amino1-propanol, 2-aminoisobutanol, 2-amino-1-butanol, 2-(2-aminoethoxy)-ethanol, and 2-aminocyclohexanol.

Although a conventionally known alcohol may be used, a C1-10 monoalcohol is preferably used. Specific examples thereof include methanol, ethanol, propanol, butanol, pentanol, hexanol, octanol, decanol, cyclopentanol, and cyclohexanol. In the case where the compound contains an isomer, the isomer may be used.

<Carbamic Acid Ester>

A carbamic acid ester obtained by conducting the method according to the present embodiment using the inorganic acid salt of an amino acid ester is a carbamic acid ester of the above-mentioned formula (C). The carbamic acid ester is specifically formed by replacing an amino group (—NH$_2$) constituting an amino acid ester of the above-shown formula with a carbamate group (—NHCOO—R'). $R^1$ is a group defined for the formula (C).

<<Basic Compound>>

It is supposed that a basic compound available in the present embodiment exhibits effects of increasing the reactivity of an amino group of an amino acid derivative by neutralizing an inorganic acid forming an inorganic acid salt of an amino acid derivative. From such a viewpoint, an inorganic base such as an alkali metal hydroxide, or an alkaline-earth metal hydroxide, or an organic base such as ammonia, amine, or phosphazenes is used as the basic compound.

Among these, an organic amine is preferable, and, in the case of an aliphatic amine, a secondary aliphatic amine or a tertiary aliphatic amine is more preferable.

The aliphatic amine is an amine having at least one aliphatic group, and the carbon number of the aliphatic group is preferably 1 to 12.

Examples of the aliphatic amine include amines formed by substituting at least one hydrogen atom of ammonia NH$_3$ with an alkyl group or a hydroxy alkyl group, the carbon number of which is 12 or less, (alkylamine or alkyl alcohol amine), and cyclic amines.

Specific examples of the alkylamine and the alkyl alcohol amine include: monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-pentylamine (triamylamine), tri-n-hexylamine, tri-n-heptylamine, tri-n-octylamine, tri-n-nonylamine, tri-n- decylamine, and tri-n-dodecylamine; alkyl alcohol amines such as diethanolamine, triethanolamine, diisopropanolamine, triisopropanolamine, di-n-octanolamine, and tri-n-octanolamine. Among these, a C5-10 trialkylamine is further preferable, and triethylamine, tri-n-pentylamine or tri-n-octylamine are particularly preferable.

Examples of the cyclic amine include heterocyclic compounds containing a nitrogen atom as a hetero atom. The heterocyclic compounds may be monocyclic (aliphatic monocyclic amines), or polycyclic (aliphatic polycyclic amines).

Specific examples of the aliphatic monocyclic amine include piperidine and piperazine. The aliphatic polycyclic amine preferably has a carbon number of 6 to 10, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

An aromatic amine may be used as an amine. Examples of the aromatic amine include 4-dimethylaminopyridine, pyrrole, indole, pyrazole, imidazole or derivatives thereof, tribenzylamine, 2,6-diisopropylaniline, and N-tert-butoxycarbonylpyrrolidine.

<<Acid Used in Washing Step (Washing Solvent)>>

Although an acid to be used in a washing step is not particularly limited, provided that the acid can dissolve the polymeric by-product, and any of organic acids and inorganic acids may be used, an organic acid is preferably used.

Although examples of the organic acid include carboxylic acids, sulfonic acids, sulfinic acids, phenols, enols, thiophenols, imides, oximes, and aromatic sulfone amides, carboxylic acids such as benzoic acid or salicylic acid, and phenols (such as phenols which may have a substituent such as a C1-20 (preferably C1-12) alkyl group, a benzyl group which may be substituted with a C1-6 alkyl group, a C1-20 (preferably C1-6) alkoxy group, or a phenol which may have a phenyl group) are preferably used. Among the organic acids, aromatic hydroxy compounds, more preferably compounds similar to aromatic hydroxyl compounds used in the reaction of a diaryl carbonate and an inorganic acid salt of an amino acid derivative, are preferably used, in view of influences exerted when the washing solvent remains after washing a formula decomposition reactor.

In the case where an aromatic hydroxy compound is used as an acid to conduct washing, the difference in the standard boiling point between the aromatic hydroxy compound and either a compound corresponding to an isocyanate produced by the thermal decomposition reaction of the carbamic acid ester or an aromatic hydroxy compound produced by the thermal decomposition reaction of the carbamic acid ester is preferably 10° C. or more, from the viewpoint of washing effects.

EXAMPLES

Next, the present invention will be explained further specifically by showing examples. However, the present invention is not be intended to be limited to the examples.

<Analysis Methods>

1) NMR Analysis Method

Equipment: JNM-A400 FT NMR system manufactured by JEOL Ltd., Japan.

(1) Preparation of Samples of 1H and 13C-NMR Analysis

Approximately 0.3 g of a sample solution was weighed, and then approximately 0.7 g of deuterated chloroform (manufactured by Aldrich, United States, 99.8%) and 0.05 g of tetramethylsilane as an internal standard substance (manufactured by Wako Pure Chemical Corporation, Japan, Wako 1$^{st}$ grade) were added to the sample solution, followed by mixing the resultant uniformly to obtain a NMR analysis sample.

(2) Quantitative Analysis Method

Each of standard substances was subjected to analysis to prepare a standard curve, and the quantitative analysis of each analysis sample solution was conducted based on the standard curve.

2) Liquid Chromatography Analysis Method

Equipment: LC-10AT system manufactured by Shimadzu Corporation, Japan.

Column: Silica-60 column manufactured by TOSOH CORPORATION, Japan, two columns were series-connected.

Developing solvent: mixture liquid of hexane/tetrahydrofuran=80/20 (volume ratio)

Solvent flow rate: 2 mL/minute

Column temperature: 35° C.

Detector: R.I. (Refractometer)

(1) Liquid Chromatography Analysis Sample

Approximately 0.1 g of a sample was weighed, and then approximately 1 g of tetrahydrofuran (manufactured by Wako Pure Chemical Corporation, Japan, anhydrated) and approximately 0.02 g of bisphenol A (manufactured by Wako Pure Chemical Corporation, Japan, 1$^{st}$ grade) as an internal standard substance were added to the sample, followed by mixing the resultant uniformly to obtain a liquid chromatography analysis sample.

(2) Quantitative Analysis Method

Each of standard substances was subjected to analysis to prepare a standard curve, and the quantitative analysis of each analysis sample solution was conducted based on the standard curve.

3) Gas Chromatography Analysis Method

Equipment: GC-2010 manufactured by Shimadzu Corporation, Japan

Column: DB-1 manufactured by Agilent Technologies, United States, and having a length of 30 m, an inner diameter of 0.250 mm, and a film thickness of 1.00 μm.

Column temperature: maintained at 50° C. for 5 minutes, raised at a rate of 10° C./minute until 200° C., maintained at 200° C. for 5 minutes, and then raised at a rate of 10° C./minute until 300° C.

Detector: FID (1) Gas Chromatography Analysis Sample

Approximately 0.05 g of a sample was weighed, and then approximately 1 g of acetone (manufactured by Wako Pure Chemical Corporation, Japan, anhydrated) and approximately 0.02 g of toluene (manufactured by Wako Pure Chemical Corporation, Japan, anhydrated) as an internal standard substance were added to the sample, followed by mixing the resultant uniformly to obtain a gas chromatography analysis sample.

(2) Quantitative Analysis Method

Each of standard substances was subjected to analysis to prepare a standard curve, and the quantitative analysis of each analysis sample solution was conducted based on the standard curve.

4) Inductively Coupled Plasma Mass Spectrometry Method

Equipment: SPQ-8000 manufactured by Seiko Instrument Inc., Japan (1) Inductively Coupled Plasma Mass Analysis Sample Approximately 0.15 g of a sample was subjected to ashing with diluted sulfuric acid, and then dissolved in diluted nitric acid.

(2) Quantitative Analysis Method

Each of standard substances was subjected to analysis to prepare a standard curve, and the quantitative analysis of each analysis sample solution was conducted based on the standard curve.

Reference Example 1 Preparation of Diphenyl Carbonate

Step (I-1): Preparation of Dialkyltin Catalyst 692 g (2.78 mol) of di-n-butyltinoxide and 2000 g (27 mol) of 1-butanol (manufactured by Wako Pure Chemical Corporation, Japan) were charged in a 3000 mL egg-plant-shaped flask. The flask in which the white slurry mixture was charged was connected to an evaporator connected with an oil bath equipped with a temperature controller, a vacuum pump and a vacuum controller. An outlet of a purge valve of the evaporator was connected to a line through which a nitrogen gas flowed at ordinary pressure. The purge valve of the evaporator was closed and then the pressure in the system was reduced, followed by opening the purge valve gradually to allow nitrogen to flow in the system to recover the ordinary pressure. The temperature of the oil bath was set at 126° C., the flask was immersed in the oil bath, and then the evaporator was brought into rotation. When the flask was rotated and heated at ordinary pressure for approximately 30 minutes while conducting stirring and opening the purge valve of the evaporator, the mixture liquid was boiled and the distillation of the low-boiling component was initiated. After this condition was maintained for 8 hours, the purge valve was closed to reduce the pressure in the system gradually, and the remaining low-boiling component was distilled at a pressure of 76 kPa to 54 kPa. After the low-boiling component could not be distilled off, the flask was brought up from the oil bath. The resultant reaction liquid was transparent. Then, the flask was brought up from the oil bath, followed by opening the purge valve gradually to recover the pressure in the system to ordinary pressure. In the flask, 952 g of the reaction liquid was obtained. From the 119Sn, 1H, 13C-NMR analysis result, it was confirmed that 1,1,3,3-tetra-n-butyl-1,3-di(n-butyloxy)-distanoxane was produced at a yield of 99% based on di-n-butyltinoxide group. The same process was repeated 12-times to obtain 1,1,3,3-tetra-n-butyl-1,3-di(n-butyloxy)-distanoxane in the total amount of 11480 g.

Step (I-2): Preparation of Dibutyl Carbonate

A carbonic acid ester was produced using continuous production equipment as shown in FIG. 1. 1,1,3,3-tetra-n-butyl-1,3-di(n-butyloxy)-distanoxane produced in the step (I-1) was supplied at a rate of 4201 g/hr through a line 4 to a tower-type reactor 102 having an inner diameter of 151 nm and an effective length of 5040 mm and filled with a filler "Mellapak 750Y" (manufactured by Sulzer Chemtech Ltd., Switzerland). 1-butanol purified at a distillation column 101 was supplied to the tower-type reactor 102 at a rate of 24717 g/hr through a line 2. In the tower-type reactor 102, the liquid temperature was maintained at 160° C. using a heater and a reboiler 112, and the pressure was maintained at approximately 150 kPa-G using a pressure control valve. The retention time in the tower-type reactor 102 was approximately 10 minutes. The 1-butanol containing water was transported to the distillation column 101 from an upper portion of the tower-type reactor 102 through a line 6 at a rate of 24715 g/hr. The 1-butanol was transported to the distillation column 101 from a line 1 at a rate of 824 g/hr. The distillation column 101 was filled with a filler "Metal Gauze CY" (manufactured by Sulzer Chemtech Ltd., Switzerland), and equipped with a reboiler 111 and a condenser 121, and the distillation and purification was conducted therein. In the upper portion of the distillation column 101, a distillation fraction containing a high concentration of water was condensed by the condenser 121, and then collected from a line 3. The purified 1-butanol was transported to the tower-type reactor 102 through the line 2 existing in the bottom of the distillation column 101. An alkyltin alkoxide catalyst composition containing di-n-butyltin di-n-butoxide and 1,1,3,3-tetra-n-butyl-1,3-di(n-butyloxy)-distanoxane was obtained from the bottom of the tower-type reactor 102, and supplied to a thin-film evaporator 103 (manufactured by KOBELCO ECO-SOLUTIONS CO., LTD., Japan) through a line 5. In the thin-film evaporator 103, 1-butanol was distilled off, and then the evaporation residue was brought back to the tower-type reactor 102 through a condenser 123, a line 8 and the line 4. The alkyltin alkoxide catalyst composition was transported from the bottom of the thin-film evaporator 103 through a line 7 to an autoclave 104 while controlling the flow rate of active components of dibutyltin dibutoxide and 1,1,3,3-tetra-n-butyl-1,3-di(n-butyloxy)-distanoxane at approximately 4812 g/hr. Carbon dioxide was supplied to the autoclave through a line 9 at a rate of 973 g/hr, and the pressure in the autoclave was maintained at 4 MPa-G The temperature in the autoclave was set at 120° C., and the retention time was controlled at approximately 4 hours, to allow the reaction of carbon dioxide and the alkyltin alkoxide catalyst composition to proceed, and thus a reaction liquid containing dibutyl carbonate was obtained. The reaction liquid was transferred to the carbon removing tank 105 through a line 10 and a control valve to remove the remaining carbon dioxide, and then carbon dioxide was collected from a line 11. Then, the reaction liquid was transported through a line 12 to a thin-film evaporator 106 (manufactured by KOBELCO ECO-SOLUTIONS CO., LTD., Japan) in which the temperature was set at 140° C. and the pressure was set at approximately 1.4 kPa, and 1,1,3,3-tetra-n-butyl-1,3-di(n-butyloxy)-distanoxane was supplied thereto while controlling the flow rate at approximately 4201 g/hr to obtain a distillation fraction containing dibutyl carbonate. On the other hand, the evaporation residue was circulated to the tower-type reactor 102 through a line 13 and the line 4 while controlling the flow rate of 1,1,3,3-tetra-n-butyl-1,3-di(n-butyloxy)-distanoxane at approximately 4201 g/hr. The distillation fraction containing dibutyl carbonate was supplied through a condenser 126 and a line 14 to a distillation column 107 filled with a filler "Metal Gauze CY" (manufactured by Sulzer Chemtech Ltd., Switzerland) and equipped with a reboiler 117 and a condenser 127 at a rate of 830 g/hr, to conduct distillation purification, and thus 99% by mass of dibutyl carbonate was obtained at a rate of 814 g/hr from a line 15. The evaporation residue transported from thin-film distillation equipment 106 to the line 13 was subjected to 119Sn, 1H, 13C-NMR analysis to confirm that 1,1,3,3-tetra-n-butyl-1,3-di(n-butyloxy)-distanoxane was contained therein, but di-n-butyltin di-n-butoxide was not contained therein. After the above-mentioned continuous operation was conducted for approximately 600 hours, the evaporation residue was exhausted from a line 16 at a rate of 16 g/hr. On the other hand, 1,1,3,3-tetra-n-butyl-1,3-di(n-butyloxy)-distanoxane produced in the step (I-1) was supplied from a line 17 at a rate of 16 g/hr.

Step (1-3): Preparation of Aromatic Carbonic Acid Ester [Preparation of Catalyst]

79 g of phenol and 32 g of lead monoxide were heated at 180° C. for 10 hours to distill away the produced water with phenol. Approximately 2.5 g of water was distilled away for 10 hours. Then, phenol was distilled away from the upper portion of the reactor to obtain a catalyst.

[Preparation of Aromatic Carbonic Acid Ester]

Figure 2:
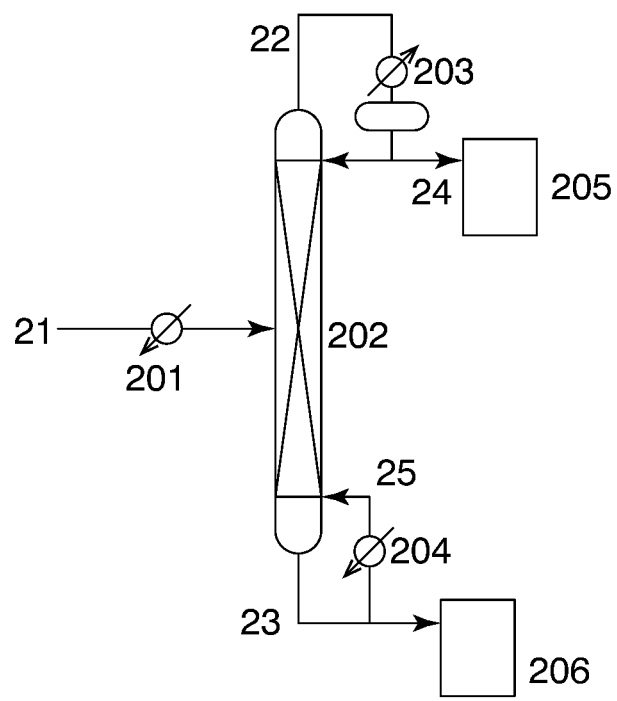
FIG. 2 indicates first equipment used in Step (I-3) in Reference Example 1.

Equipment shown in FIG. 2 was used.

A mixture liquid composed of the dibutyl carbonate obtained in the step (I-2), a phenol, and the catalyst prepared as mentioned above (prepared such that the mass ratio of the dibutyl carbonate and phenol became approximately 65/35, and the concentration of lead became approximately 1% by mass) was supplied continuously to the middle stage of a continuous multistage distillation column 202 having an inner diameter of approximately 5 cm and a column length of 2 m and filled with dixon packings (6 mmφ) through a preheater 201 from a line 21 at a rate of approximately 270 g/hr in a liquid state to conduct reaction. The heat quantity required to conduct reaction and distillation was supplied by circulating a liquid at the bottom of the continuous multistage distillation column 202 through a line 23 and a reboiler 204. The reflux flow rate from a line 24 to the continuous multistage distillation column 202 was controlled such that the liquid temperature at the bottom of the continuous multistage distillation column 202 became 238° C., the pressure at the top thereof became approximately 250 kPa, and the reflux ratio became approximately 2. A gas distilled off from the top of the continuous multistage distillation column 202 was exhausted from a line 22, and transported through a condenser 203 to a storage tank 205 continuously from a line 24 at approximately 67 g/hr. From the bottom of the column, the resultant was transported through a line 23 to a storage tank 206 at approximately 204 g/hr continuously.

The liquid composition transported from the line 24 was composed of approximately 33% by mass of 1-butanol, approximately 65% by mass of phenol, and approximately 2% by mass of dibutyl carbonate. The liquid composition transported to the storage tank 206 was composed of approximately 11% by mass of phenol, approximately 60% by mass of dibutyl carbonate, approximately 26% by mass of butylphenyl carbonate, approximately 1.6% by mass of diphenyl carbonate, and approximately 1% by mass of lead.

Figure 3:
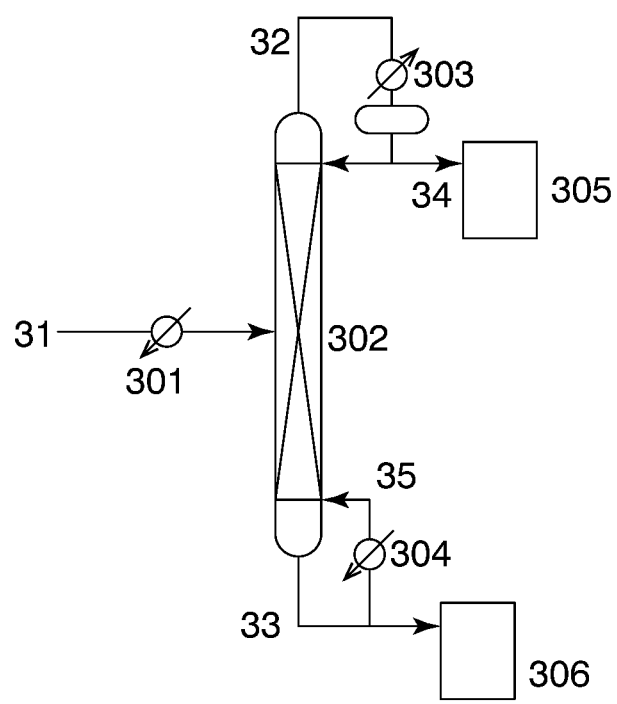
FIG. 3 indicates second equipment used in Step (I-3) in Reference Example 1.

Next, equipment as shown in FIG. 3 was used.

The liquid transported to the storage tank 206 was supplied continuously to the middle stage of a continuous multistage distillation column 302 having an inner diameter of approximately 5 cm and a column length of 2 m and filled with dixon packings (6 mmφ) through a preheater 301 from a line 31 at a rate of approximately 203 g/hr in a liquid state to conduct reaction. The heat quantity required to conduct reaction and distillation was supplied by circulating a liquid at the bottom of the continuous multistage distillation column 302 through a line 33 and a reboiler 304. The reflux flow rate from a line 34 to the continuous multistage distillation column 302 was controlled such that the liquid temperature at the bottom of the continuous multistage distillation column 302 became 240° C., the pressure at the top thereof became approximately 27 kPa, and the reflux ratio became approximately 2. A gas distilled off from the top of the continuous multistage distillation column 302 was transported through a line 32 to a condenser 303 to conduct condensation, and then transported to a storage tank 305 continuously from a line 34 at approximately 165 g/hr. From the bottom of the column, the resultant was transported through a line 33 to a storage tank 306 at approximately 39 g/hr continuously.

The liquid composition transported from the line 34 was composed of approximately 500 ppm by mass of 1-butanol, approximately 13% by mass of phenol, approximately 85% by mass of dibutyl carbonate, and approximately 2% by mass of butylphenyl carbonate. The liquid composition transported to the storage tank 306 was composed of approximately 0.3% by mass of dibutyl carbonate, approximately 32% by mass of butylphenyl carbonate, approximately 61% by mass of diphenyl carbonate, and approximately 7% by mass of lead.

[Recycle of Alcohol]

Figure 4:
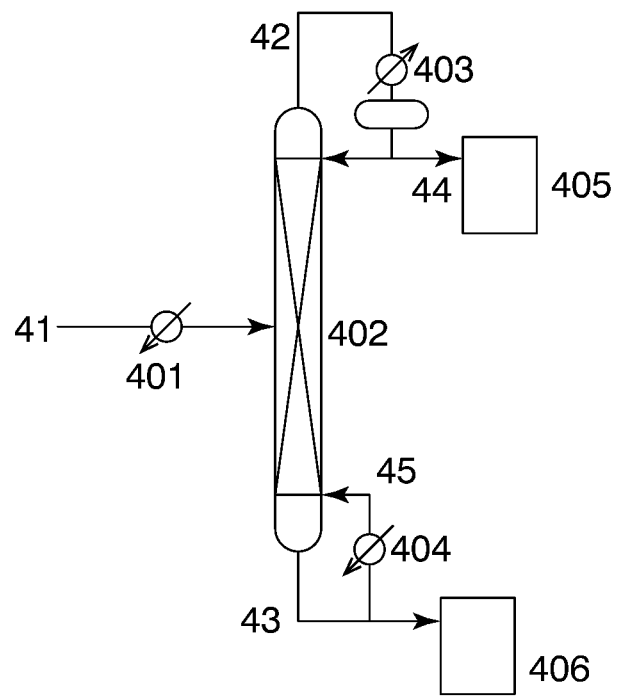
FIG. 4 indicates third equipment used in Step (I-3) in Reference Example 1.

Equipment shown in FIG. 4 was used to recycle alcohol.

The liquid transported continuously to the storage tank 205 at the above-mentioned step was supplied continuously to a continuous multistage distillation column 402 having an inner diameter of approximately 5 cm and a column length of 2 m and filled with dixon packings (6 mmφ) from the position locating at 0.7 cm above the lowest part of the column through a line 41 and then a preheater 401 at approximately 201 g/hr, to conduct distillation separation. The heat quantity required to conduct distillation separation was supplied by circulating the liquid at the bottom of the continuous multistage distillation column 402 through a line 43 and a reboiler 404. The liquid temperature at the bottom of the continuous multistage distillation column 402 was 145° C., the pressure at the top thereof was approximately 13 kPa, and the reflux ratio was approximately 0.3. A gas distilled off from the continuous multistage distillation column 402 was transported through a line 42 to a condenser 403 to conduct condensation, and then transported to a storage tank 405 from a line 44 at approximately 68 g/hr. From the bottom of the column, the resultant was transported through a line 43 to a storage tank 406 at approximately 133 g/hr continuously.

The liquid composition transported from the line 44 was composed of approximately 99% by mass of 1-butanol, and approximately 100 ppm by mass of phenol. The liquid composition transported to the storage tank 406 was composed of approximately 2% by mass of dibutyl carbonate and approximately 98% by mass of phenol.

[Purification of Diaryl Carbonate]

Figure 5:
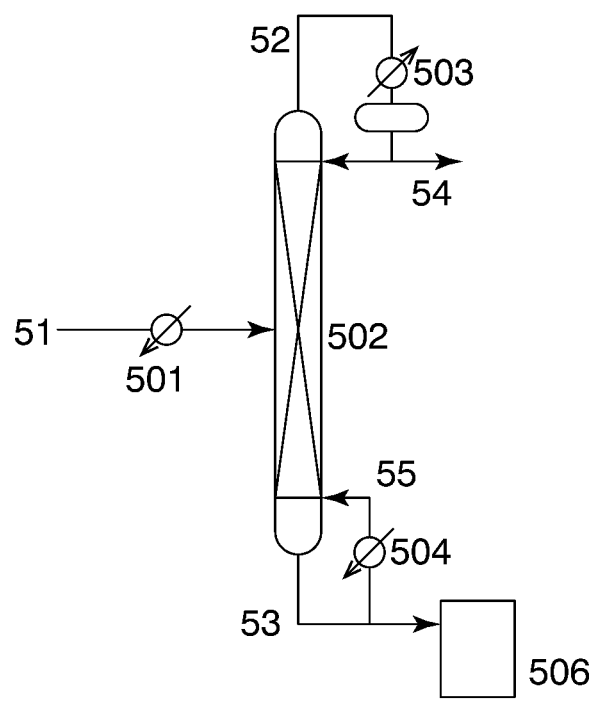
FIG. 5 indicates fourth equipment used in Step (I-3) in Reference Example 1.
Figure 6:
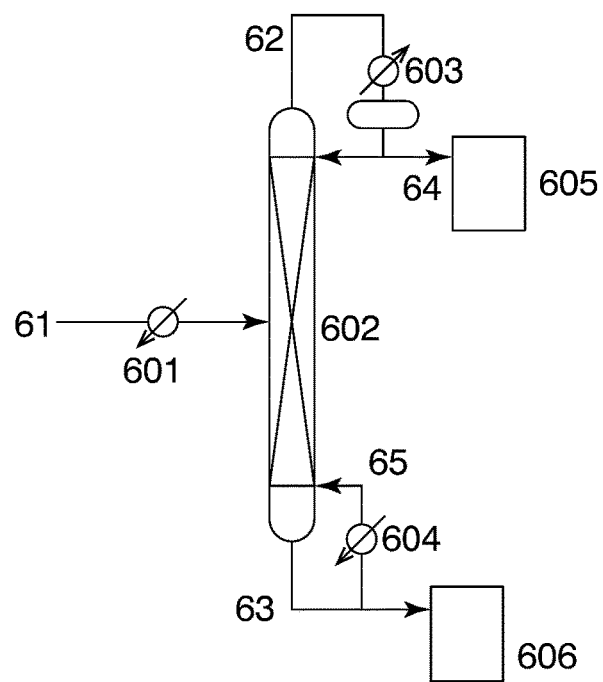
FIG. 6 indicates fifth equipment used in Step (I-3) in Reference Example 1.

Equipment shown in FIGS. 5 and 6 were used to purify diaryl carbonate.

The liquid transported to the storage tank 306 was continuously supplied to the middle stage of a continuous multistage distillation column 502 having an inner diameter of approximately 5 cm and a column length of 2 m and filled with dixon packings (6 mmφ) through a line 51 and then a preheater 501 at approximately 195 g/hr. The heat quantity required to conduct distillation purification was supplied by circulating the liquid at the bottom of the continuous multistage distillation column 502 through a line 53 and a reboiler 504. The liquid temperature at the bottom of the continuous multistage distillation column 502 was 210° C., the pressure at the top thereof was approximately 1.5 kPa, and the reflux ratio was approximately 1. A gas distilled off from the continuous multistage distillation column 502 was transported through a line 52 to a condenser 503 to conduct condensation, and then exhausted from a line 54 continuously. From the bottom of the column, the resultant was transported through a line 53 to a storage tank 506 at approximately 14 g/hr.

The liquid composition transported from the line 54 was composed of approximately 0.3% by mass of dibutyl carbonate, approximately 34% by mass of butylphenyl carbonate, and approximately 66% by mass of diphenyl carbonate.

The liquid exhausted from the line 54 was supplied to the middle stage of a continuous multistage distillation column 602 having an inner diameter of approximately 5 cm and a column length of 2 m and filled with dixon packings (6 mmφ) through a line 61 and then a preheater 601 at approximately 181 g/hr continuously. The heat quantity required to conduct distillation separation was supplied by circulating the liquid at the bottom of the continuous multistage distillation column 602 via a line 63 and a reboiler 604. The liquid temperature at the bottom of the continuous multistage distillation column 602 was 232° C., the pressure at the top thereof was approximately 15 kPa, and the reflux ratio was approximately 2. A gas distilled off from the top of the continuous multistage distillation column 602 was transported through a line 62 to a condenser 603 to conduct condensation, and then transported from a line 64 to a storage tank 605 continuously. From the bottom of the column, the resultant was transported through a line 63 to a storage tank 606 at approximately 119 g/hr.

The liquid composition transported from the line 64 was composed of approximately 0.6% by mass of dibutyl carbonate, approximately 99% by mass of butylphenyl carbonate, and approximately 0.4 by mass of diphenyl carbonate. The liquid composition transported to the storage tank 606 was composed of 0.1% by mass of butylphenyl carbonate and approximately 99.9% by mass of diphenyl carbonate. The diphenyl carbonate contained 22 ppm by mass of iron as a metallic component.

Example 1

Precursor Preparation Step: Synthesis of Lysine β-Aminoethyl Ester Trihydrochloride 313 g (3.0 mol) of 35% by mass of hydrochloric acid was charged in a 1 L four-necked flask equipped with a stirrer, cooled in an ice bath, and then 122 g (2.0 mol) of ethanolamine was added dropwise thereto slowly. Then, 183 g (1.0 mol) of lysine monohydrochloride was added thereto. The pressure in the reactor was made to be 4 kPa, the reaction liquid was heated to 110° C., and then 200 g of water in the reaction liquid was distilled off.

(Step A)

A xylene gas heated to 110° C. at a pressure of 4 kPa using a preheater was supplied to the reactor in which the pressure was maintained at 4 kPa and the reaction liquid temperature was maintained at 110° C. from the bottom of the reaction liquid. The flow rate of the xylene gas was 18 g/hr. Xylene and water were distilled off from the reaction system while supplying a xylene gas thereto to make the amount of water in the reaction liquid be 0.4% by mass or less The resultant reaction liquid was charged in a 500 mL flask equipped with a stirrer, the reaction liquid temperature was made to be 110° C., and a hydrogen chloride gas was supplied thereto under ordinary pressure such that the content thereof, relative to the mass of the reaction liquid, became 1.0% by mass.

The above-mentioned step A was further repeated twice to obtain a reaction liquid in which the esterification rate was 80%.

The esterification rate was calculated in accordance with the following formula.

Esterification rate (%)=$X/Y \times 100$

In the formula, X represents the molar number of the produced lysine β-aminoethyl ester trihydrochloride (value quantitated by analysis using high speed liquid chromatography) and Y represents the molar number of lysine monohydrochloride used as a raw material.

(Step B)

A mixture liquid composed of 720 g of methanol and 480 g of ortho-dichlorobenzene was added to the reaction liquid obtained in the step A, and then dissolved therein, followed by adding a small amount of seed crystal to the solution to conduct crystallization. The solid was filtered off, washed with a methanol/ortho-dichlorobenzene mixture liquid having the same constitution as that used to conduct crystallization, and then filtered off. The solid was dried using a reduced-pressure drier, and then analyzed by liquid chromatography to confirm that lysine β-aminoethyl ester trihydrochloride was obtained.

Carbamation Step: Preparation of Carbamic Acid Ester (Carbamate)

510 g (2.4 mol) of diphenyl carbonate, 136 g (1.35 mol) of triethylamine, and 150 g (0.34 mol) of the lysine β-aminoethyl ester trihydrochloride obtained in the precursor preparation step were reacted in toluene at 50° C. in ordinary pressure for 8 hours under a nitrogen atmosphere in a 1 L four-necked flask equipped with a stirrer. Samplings of the reaction liquid were taken to conduct analysis by liquid chromatography, and, as a result of which, it was confirmed that a target carbamic acid ester was produced. After 1 mol/L of hydrochloric acid was added to the reaction liquid and then the mixture was stirred, an organic layer was collected, and then the organic layer was washed with ion-exchanged water.

Toluene was distilled off from the organic layer using a rotary evaporator to obtain a solid, and then the solid was analyzed by 1H-NMR, and, as a result of which, it was confirmed that the solid was 2-((phenoxycarbonyl)amino) ethyl-2,6-bis((phenoxycarbonyl)amino) hexanoate.

Step of Blending Starting Materials

Step of blending starting materials: 500 g (0.91 mol) of 2-((phenoxycarbonyl)amino)ethyl-2,6-bis((phenoxycarbonyl)amino)hexanoate obtained in the carbamation step and 500 g of phenol were mixed at 60° C. in a storage tank 700 to obtain a uniform mixture liquid.

Figure 7:
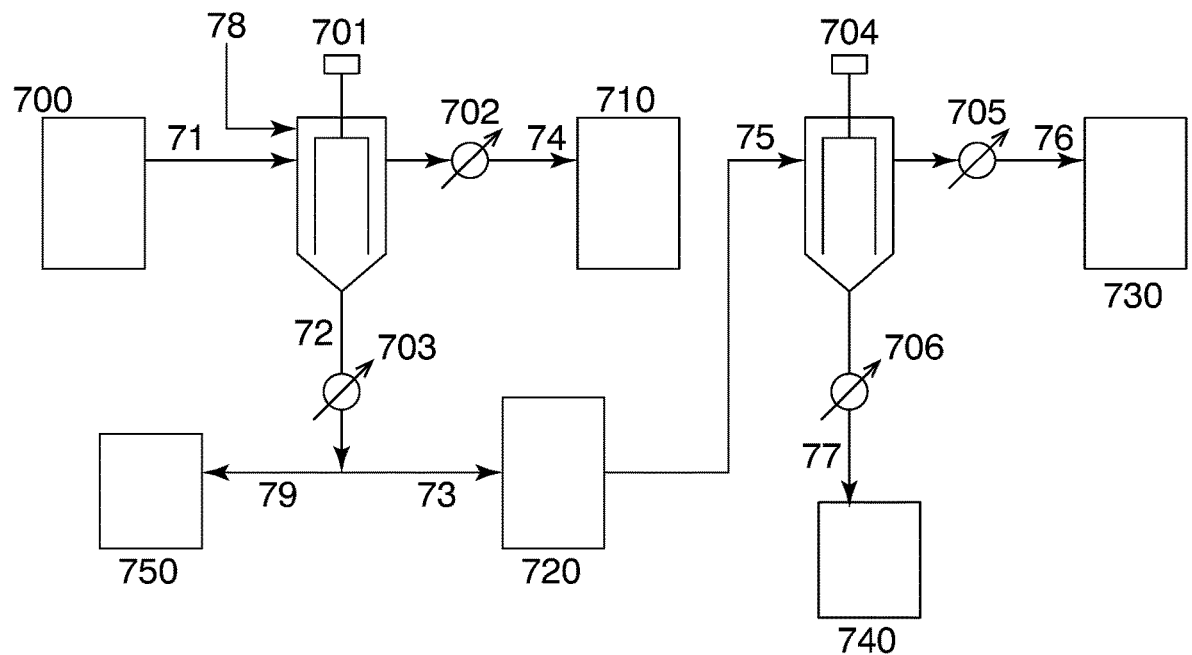
FIG. 7 indicates thin-film distillation equipment used in examples.

Thermal decomposition step and separation step: Preparation of lysine ester triisocyanate by thermal decomposition of 2-((phenoxycarbonyl)amino)ethyl-2,6-bis((phenoxycarbonyl)amino)hexanoate Tin-film distillation equipment 701 having a heat-transfer area of 0.1 m², as shown in FIG. 7, was heated at 270° C., and the internal pressure was made to be 10 kPa. A starting material was supplied to the thin-film distillation equipment 701 at 500 g/hr from a storage tank 700 using a line 71, and the resultant liquid (high-boiling-point component) was collected from the bottom of the thin-film distillation equipment 701 through a line 72, and then cooled to 100° C. in cooling equipment 703, followed by collecting the resultant in a storage tank 720 using a line 73. A vapor of a low-boiling-point component collected from the upper portion of the thin-film distillation equipment 701 was condensed by a condenser 702, and then collected in a storage tank 710 using a line 74.

Next, the liquid collected in the storage tank 720 was supplied using a line 75 at 250 g/hr to thin-film distillation equipment 704 having a heat-transfer area of 0.1 m², heated at 180° C., and made the internal pressure to be approximately 0.05 kPa. The temperature (temperature at the transfer step) when the liquid was transferred from the storage tank 720 to the thin-film distillation equipment 704 using the line 75 was 130° C. The gas phase component (low-boiling-point component contained in the high-boiling point component) produced from the thin-film distillation equipment 704 was condensed in a condenser 705, and collected using a line 76 in a storage tank 730. A high-boiling-point component obtained by removing the low-boiling-point component contained in the high-boiling point component was cooled at 80° C. in a cooling equipment 706, and then collected using a line 77 in a storage tank 740. The collected liquid collected in the storage tank 730 was analyzed by 1H and 13C-NMR and gas chromatography (GC), and, as a result of which, it was confirmed that the collected liquid was lysine ester triisocyanate. The yield based on lysine β-aminoethyl ester trihydrochloride was 70%. When the continuous operation was conducted for 10 days, no adhesion was confirmed on the wall surface of the thin-film distillation equipment 701.

Examples 2 to 57

Operations were conducted under the same conditions as described in Example 1, except that the lysine in Example 1 was replaced with an equimolar amount of each amino acid, and each gas phase component was condensed and collected. An alcohol was added in a molar amount corresponding to the number of carboxyl groups in each amino acid (involving derivatives). In the case where a carbamic acid ester was obtained in each example, a carbonic acid ester was added in a molar amount corresponding to the number of amino groups in each amino acid (involving derivatives) to allow the reaction to proceed. Components contained in the collected liquid were analyzed by 1H-NMR and 13C-NMR and GC, and, as a result of which, it was confirmed that the collection liquid was an amino acid ester isocyanate corresponding to each amino acid (involving derivatives). The yield (%) and the behavior of adhesions are shown in the following tables. In the item "abbreviation" in "carbonic acid ester" in the tables, DPC means diphenyl carbonate, DMC means dimethyl carbonate, DEC means diethyl carbonate, and DBC means di(n-butyl) carbonate. In the case where arginine was used, the arginine was decomposed to ornithine by a conventionally known method to be used. In the case where glutamine or asparagine was used, the glutamine or the asparagine was hydrolyzed to glutamic acid or asparaginic acid, respectively, by a conventionally known method.

TABLE 1

| | Raw material of amino acid derivative | | | Carbonic acid ester | | | | Result of carbamation reaction | | | Adhesion in thin film distillation equipment |
|---|---|---|---|---|---|---|---|---|---|---|---|
| | Amino acid | $NH_2$ group number | COOH group number | Alcohol | Abbreviation | Metallic component in carbonic acid ester | Metallic amount (ppm by mass) | Base | Esterification efficiency | Carbamation yield | Thermal decomposition yield | by thermal decomposition of carbamate After 10 days |
| Example 1 | Lysine | 2 | 1 | Monoethanolamine | DPC | Fe | 22 | Triethylamine | 80 | 93 | 70 | Absence |
| Example 2 | Alanine | 1 | 1 | Monoethanolamine | DPC | Fe | 22 | Triethylamine | 81 | 87 | 70 | Absence |
| Example 3 | Arginine | 2 | 1 | Monoethanolamine | DPC | Fe | 22 | Triethylamine | 71 | 93 | 68 | Absence |
| Example 4 | Asparagine | 2 | 1 | Monoethanolamine | DPC | Fe | 22 | Triethylamine | 77 | 83 | 67 | Absence |
| Example 5 | Glutamine | 2 | 1 | Monoethanolamine | DPC | Fe | 22 | Triethylamine | 74 | 93 | 68 | Absence |
| Example 6 | Glycine | 1 | 1 | Monoethanolamine | DPC | Fe | 22 | Triethylamine | 79 | 86 | 66 | Absence |
| Example 7 | Asparaginic acid | 1 | 2 | Monoethanolamine | DPC | Fe | 22 | Triethylamine | 70 | 85 | 64 | Absence |
| Example 8 | Glutamic acid | 1 | 2 | Monoethanolamine | DPC | Fe | 22 | Triethylamine | 70 | 89 | 62 | Absence |
| Example 9 | Histidine | 1 | 1 | Monoethanolamine | DPC | Fe | 22 | Triethylamine | 68 | 86 | 69 | Absence |
| Example 10 | Isoleucine | 1 | 1 | Monoethanolamine | DPC | Fe | 22 | Triethylamine | 75 | 87 | 66 | Absence |
| Example 11 | Leucine | 1 | 1 | Monoethanolamine | DPC | Fe | 22 | Triethylamine | 77 | 87 | 68 | Absence |
| Example 12 | Methionine | 1 | 1 | Monoethanolamine | DPC | Fe | 22 | Triethylamine | 70 | 85 | 67 | Absence |
| Example 13 | Phenylalanine | 1 | 1 | Monoethanolamine | DPC | Fe | 22 | Triethylamine | 72 | 87 | 62 | Absence |
| Example 14 | Triptophan | 1 | 1 | Monoethanolamine | DPC | Fe | 22 | Triethylamine | 69 | 86 | 70 | Absence |
| Example 15 | Valine | 1 | 1 | Monoethanolamine | DPC | Fe | 22 | Triethylamine | 74 | 86 | 67 | Absence |

TABLE 2

| | Raw material of amino acid derivative | | | | | | | | |
|---|---|---|---|---|---|---|---|---|---|
| | Amino acid | Formula | x | Ra | Rb | Explanation of formula | $NH_2$ group number | COOH group number | Alcohol |
| Example 16 | Ornithine | $H_2N\text{-}...\text{-}CH(NH_2)\text{-}COOH$ | — | — | — | — | 2 | 1 | Mono-ethanol-amine |
| Example 17 | Glutamic acid derivative | $R^a\text{-}[O\text{-}C(=O)\text{-}...\text{-}CH(NH_2)\text{-}C(=O)\text{-}O\text{-}R^b]_x$ | 1 | Me | H | Ra and Rb each independenly represents an aliphatic group, an aromatic group, or a hydrogen atom, X = 1-4 (excepting that Ra represents a hydrogen atom). When both Ra and Rb represent hydrogen atoms, x represents 1. | 1 | 1 | Mono-ethanol-amine |
| Example 18 | Glutamic acid derivative | $R^a\text{-}[O\text{-}C(=O)\text{-}...\text{-}CH(NH_2)\text{-}C(=O)\text{-}O\text{-}R^b]_x$ | 2 | Me | H | Ra and Rb each independenly represents an aliphatic group, an aromatic group, or a hydrogen atom, X = 1-4 (excepting that Ra represents a hydrogen atom). When both Ra and Rb represent hydrogen atoms, x represents 1. | 2 | 1 | Mono-ethanol-amine |
| Example 19 | Glutamic acid derivative | $R^a\text{-}[O\text{-}C(=O)\text{-}...\text{-}CH(NH_2)\text{-}C(=O)\text{-}O\text{-}R^b]_x$ | 1 | Me | H | Ra and Rb each independenly represents an aliphatic group, an aromatic group, or a hydrogen atom, X = 1-4 (excepting that Ra represents a hydrogen atom). When both Ra and Rb represent hydrogen atoms, x represents 1. | 1 | 1 | Mono-ethanol-amine |

| | Carbonic acid ester | | | | Result of carbamation reaction | | | Adhesion in thin film distillation equipment by thermal decomposition of carbamate After 10 days |
|---|---|---|---|---|---|---|---|---|
| | Abbreviation | Metallic component in carbonic acid ester | Metallic amount (ppm by mass) | Base | Esterification efficiency (%) | Carbamation yield (%) | Thermal decomposition yield (%) | |
| Example 16 | DPC | Fe | 22 | Triethyl-amine | 78 | 85 | 60 | Absence |
| Example 17 | DPC | Fe | 22 | Triethyl-amine | 70 | 88 | 58 | Absence |
| Example 18 | DPC | Fe | 22 | Triethyl-amine | 70 | 93 | 57 | Absence |
| Example 19 | DPC | Fe | 22 | Triethyl-amine | 69 | 87 | 56 | Absence |

TABLE 3

| | | Raw material of amino acid derivative | | | | | | |
|---|---|---|---|---|---|---|---|---|
| | Amino acid | Formula | x | Ra | Rb | Explanation of formula | $NH_2$ group number | COOH group number |
| Example 20 | Methionine derivative | [structure: $H_2N$–CH(CH$_2$CH$_2$SCH$_3$)–C(=O)–O–$R^a$]$_x$ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, x represents 1. | 1 | 0 |
| Example 21 | Glycine derivative | [structure: $H_2N$–CH$_2$–C(=O)–O–$R^a$]$_x$ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, x represents 1. | 1 | 0 |
| Example 22 | Phenylalanine derivative | [structure: $H_2N$–CH(CH$_2$Ph)–C(=O)–O–$R^a$]$_x$ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, x represents 1. | 1 | 0 |
| Example 23 | Asparaginic acid derivative | [structure: $R^b$–O–C(=O)–CH$_2$–CH($NH_2$)–C(=O)–O–$R^a$]$_x$ | 1 | Me | H | Ra and Rb each independently represents an aliphatic group, an aromatic group, or a hydrogen atom, X = 1-4 (excepting that Ra represents a hydrogen atom). When both Ra and Rb represent hydrogen atoms, x represents 1. | 1 | 0 |

| | Carbonic acid ester | | | | Result of carbamation reaction | | | Adhesion in thin film distillation equipment by thermal decomposition of carbamate After 10 days |
|---|---|---|---|---|---|---|---|---|
| | Abbreviation | Metallic component in carbonic acid ester | Metallic amount (ppm by mass) | Base | Esterification efficiency (%) | Carbamation yield (%) | Thermal decomposition yield (%) | |
| Example 20 | DPC | Fe | 22 | Triethylamine | 71 | 83 | 62 | Absence |
| Example 21 | DPC | Fe | 22 | Triethylamine | 74 | 92 | 63 | Absence |
| Example 22 | DPC | Fe | 22 | Triethylamine | 68 | 82 | 61 | Absence |
| Example 23 | DPC | Fe | 22 | Triethylamine | 66 | 91 | 59 | Absence |

TABLE 4

| | | Raw material of amino acid derivative | | | | | | |
|---|---|---|---|---|---|---|---|---|
| | Amino acid | Formula | x | Ra | Rb | Explanation of formula | $NH_2$ group number | COOH group number |
| Example 24 | Alanine derivative | $\left[ H_2N-CH(CH_3)-C(=O)-O \right]_x R^a$ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, x represents 1. | 1 | 0 |
| Example 25 | Leucine derivative | $\left[ H_2N-CH(CH_2CH(CH_3)_2)-C(=O)-O \right]_x R^a$ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, x represents 1. | 1 | 0 |
| Example 26 | Isoleucine derivative | $\left[ H_2N-CH(CH(CH_3)CH_2CH_3)-C(=O)-O \right]_x R^a$ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, x represents 1. | 1 | 0 |
| Example 27 | Valine derivative | $\left[ H_2N-CH(CH(CH_3)_2)-C(=O)-O \right]_x R^a$ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, x represents 1. | 1 | 0 |

| | Carbonic acid ester | | | | Result of carbamation reaction | | | Adhesion in thin film distillation equipment by |
|---|---|---|---|---|---|---|---|---|
| | Abbreviation | Metallic component in carbonic acid ester | Metallic amount (ppm by mass) | Base | Esterification efficiency (%) | Carbamation yield (%) | Thermal decomposition yield (%) | thermal decomposition of carbamate After 10 days |
| Example 24 | DPC | Fe | 22 | Triethylamine | 68 | 88 | 58 | Absence |
| Example 25 | DPC | Fe | 22 | Triethylamine | 69 | 85 | 61 | Absence |
| Example 26 | DPC | Fe | 22 | Triethylamine | 68 | 85 | 64 | Absence |
| Example 27 | DPC | Fe | 22 | Triethylamine | 66 | 85 | 61 | Absence |

TABLE 5

| | | Raw material of amino acid derivative | | | | | | |
|---|---|---|---|---|---|---|---|---|
| | Amino acid | Formula | x | Ra | Rb | Explanation of formula | $NH_2$ group number | COOH group number |
| Example 28 | Synthesized amino acid | [structure: 1,3,5-trisubstituted benzene with three $-CH(NH_2)-C(=O)-O-R^a$ groups] | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, x represents 1. | 3 | 0 |
| Example 29 | Synthesized amino acid | [structure: $R^aO-C(=O)-CH(NH_2)-(CH_2)_4-CH(NH_2)-C(=O)-OR^a$] | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, x represents 1. | 2 | 0 |
| Example 30 | Synthesized amino acid | [structure: Cl,F-substituted phenyl-CH($NH_2$)-C(=O)-O-$R^a$] | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, x represents 1. | 1 | 0 |
| Example 31 | Synthesized amino acid | [structure: 3,4-dimethoxyphenyl-CH($NH_2$)-C(=O)-O-$R^a$] | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, x represents 1. | 1 | 0 |

| | Carbonic acid ester | | | | Result of carbamation reaction | | | Adhesion in thin film distillation equipment |
|---|---|---|---|---|---|---|---|---|
| | Abbreviation | Metallic component in carbonic acid ester | Metallic amount (ppm by mass) | Base | Esterification efficiency (%) | Carbamation yield (%) | Thermal decomposition yield (%) | by thermal decomposition of carbamate After 10 days |
| Example 28 | DPC | Fe | 22 | Triethylamine | 60 | 90 | 63 | Absence |
| Example 29 | DPC | Fe | 22 | Triethylamine | 62 | 84 | 59 | Absence |

TABLE 5-continued

| | | | | | | | | |
|---|---|---|---|---|---|---|---|---|
| Example 30 | DPC | Fe | 22 | Triethyl-amine | 63 | 88 | 57 | Absence |
| Example 31 | DPC | Fe | 22 | Triethyl-amine | 61 | 88 | 61 | Absence |

TABLE 6

| | | Raw material of amino acid derivative | | | | | | |
|---|---|---|---|---|---|---|---|---|
| | Amino acid | Formula | x | Ra | Rb | Explanation of formula | NH₂ group number | COOH group number |
| Example 32 | Synthesized amino acid | 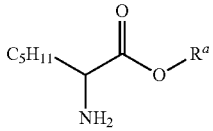 | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, x represents 1. | 1 | 0 |
| Example 33 | Synthesized amino acid | 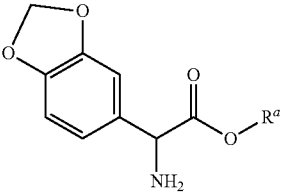 | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, x represents 1. | 1 | 0 |
| Example 34 | Synthesized amino acid | 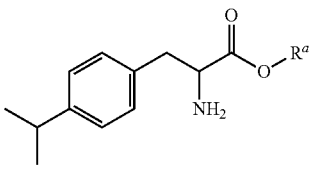 | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, x represents 1. | 1 | 0 |
| Example 35 | Synthesized amino acid | 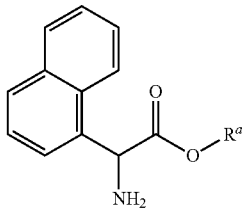 | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, x represents 1. | 1 | 0 |

TABLE 6-continued

| | | Carbonic acid ester | | | Result of carbamation reaction | | | Adhesion in thin film distillation equipment |
| --- | --- | --- | --- | --- | --- | --- | --- | --- |
| | Abbreviation | Metallic component in carbonic acid ester | Metallic amount (ppm by mass) | Base | Esterification efficiency (%) | Carbamation yield (%) | Thermal decomposition yield (%) | by thermal decomposition of carbamate After 10 days |
| Example 32 | DPC | Fe | 22 | Triethylamine | 64 | 89 | 60 | Absence |
| Example 33 | DPC | Fe | 22 | Triethylamine | 60 | 91 | 62 | Absence |
| Example 34 | DPC | Fe | 22 | Triethylamine | 61 | 88 | 64 | Absence |
| Example 35 | DPC | Fe | 22 | Triethylamine | 66 | 87 | 62 | Absence |

TABLE 7

| | Raw material of amino acid derivative | | | | | | | |
| --- | --- | --- | --- | --- | --- | --- | --- | --- |
| | Amino acid | Formula | x | Ra | Rb | Explanation of formula | $NH_2$ group number | COOH group number |
| Example 36 | Synthesized amino acid | [structure: benzene ring with two $H_2N$-CH-C(=O)-O-$R^a$ groups] | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, x represents 1. | 1 | 0 |
| Example 37 | Synthesized amino acid | [structure: furan ring with CH($NH_2$)-C(=O)-O-$R^a$ group] | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, x represents 1. | 1 | 0 |

| | Carbonic acid ester | | | | Result of carbamation reaction | | | Adhesion in thin film distillation equipment by |
| --- | --- | --- | --- | --- | --- | --- | --- | --- |
| | Abbreviation | Metallic component in carbonic acid ester | Metallic amount (ppm by mass) | Base | Esterification efficiency (%) | Carbamation yield (%) | Thermal decomposition yield (%) | thermal decomposition of carbamate After 10 days |
| Example 36 | DPC | Fe | 22 | Triethylamine | 63 | 89 | 63 | Absence |
| Example 37 | DPC | Fe | 22 | Triethylamine | 62 | 89 | 61 | Absence |

TABLE 8

| | Raw material of amino acid derivative | | | | Carbonic acid ester | | | | Result of carbamation reaction | | | Adhesion in thin film distillation equipment |
| --- | --- | --- | --- | --- | --- | --- | --- | --- | --- | --- | --- | --- |
| | Amino acid | NH$_2$ group number | COOH group number | Alcohol | Abbreviation | Metallic component in carbonic acid ester | Metallic amount (ppm by mass) | Base | Esterification efficiency (%) | Carbamation yield (%) | Thermal decomposition yield (%) | by thermal decomposition of carbamate After 10 days |
| Example 38 | Lysine | 2 | 1 | EtOH | DPC | Fe | 22 | Triethylamine | 79 | 90 | 72 | Absence |
| Example 39 | Lysine | 2 | 1 | 1-Amino-2-propanol | DPC | Fe | 22 | Triethylamine | 77 | 86 | 67 | Absence |
| Example 40 | Lysine | 2 | 1 | 2-Amino-1-butanol | DPC | Fe | 22 | Triethylamine | 73 | 91 | 66 | Absence |
| Example 41 | Lysine | 2 | 1 | Glycerine | DPC | Fe | 22 | Triethylamine | 70 | 83 | 62 | Absence |
| Example 42 | Lysine | 2 | 1 | Pentaerythritol | DPC | Fe | 22 | Triethylamine | 68 | 93 | 60 | Absence |
| Example 43 | Arginine | 2 | 1 | EtOH | DPC | Fe | 22 | Triethylamine | 71 | 82 | 68 | Absence |
| Example 44 | Arginine | 2 | 1 | 1-Amino-2-propanol | DPC | Fe | 22 | Triethylamine | 69 | 92 | 66 | Absence |
| Example 45 | Arginine | 2 | 1 | 2-Amino-1-butanol | DPC | Fe | 22 | Triethylamine | 68 | 88 | 64 | Absence |
| Example 46 | Arginine | 2 | 1 | Glycerine | DPC | Fe | 22 | Triethylamine | 64 | 86 | 60 | Absence |
| Example 47 | Arginine | 2 | 1 | Pentaerythritol | DPC | Fe | 22 | Triethylamine | 61 | 85 | 56 | Absence |
| Example 48 | Asparagine | 2 | 1 | EtOH | DPC | Fe | 22 | Triethylamine | 74 | 88 | 61 | Absence |
| Example 49 | Asparagine | 2 | 1 | 1-Amino-2-propanol | DPC | Fe | 22 | Triethylamine | 71 | 91 | 59 | Absence |
| Example 50 | Asparagine | 2 | 1 | 2-Amino-1-butanol | DPC | Fe | 22 | Triethylamine | 73 | 87 | 62 | Absence |
| Example 51 | Asparagine | 2 | 1 | Glycerine | DPC | Fe | 22 | Triethylamine | 69 | 93 | 60 | Absence |
| Example 52 | Asparagine | 2 | 1 | Pentaerythritol | DPC | Fe | 22 | Triethylamine | 62 | 89 | 54 | Absence |
| Example 53 | Glutamine | 2 | 1 | EtOH | DPC | Fe | 22 | Triethylamine | 71 | 88 | 70 | Absence |
| Example 54 | Glutamine | 2 | 1 | 1-Amino-2-propanol | DPC | Fe | 22 | Triethylamine | 67 | 87 | 64 | Absence |
| Example 55 | Glutamine | 2 | 1 | 2-Amino-1-butanol | DPC | Fe | 22 | Triethylamine | 68 | 84 | 62 | Absence |
| Example 56 | Glutamine | 2 | 1 | Glycerine | DPC | Fe | 22 | Triethylamine | 61 | 92 | 58 | Absence |
| Example 57 | Glutamine | 2 | 1 | Pentaerythritol | DPC | Fe | 22 | Triethylamine | 58 | 82 | 56 | Absence |

Examples 58 to 65

The same operations as those in Example 1 were conducted, except that carbamate corresponding to ester formed by each amino acid and alcohol was reacted with each carbonic acid ester shown in the following tables. The carbonic acid ester was added in a mole amount corresponding to the number of amino groups of the ester produced in each example. In the case where arginine was used, the arginine was decomposed to ornithine by a conventionally known method to be used. In the case where glutamine or asparagine was used, the glutamine or the asparagine was hydrolyzed to glutamic acid or asparaginic acid, respectively, by a conventionally known method.

Examples 66 to 77

The same operations as those in Example 1 were conducted, except that basic compounds shown in the following tables were used to obtain carbamates corresponding to esters formed by each of amino acids and alcohols. The basic compound was added in the same mole amount as that of Example 1. In the case where arginine was used, the arginine was decomposed to ornithine by a conventionally known method to be used. In the case where glutamine or asparagine was used, the glutamine or the asparagine was hydrolyzed to glutamic acid or asparaginic acid, respectively, by a conventionally known method.

Examples 78 to 89

The same operations as those in Example 1 were conducted, except that iron acetyl acetonate (II) was added to diphenyl carbonate of Reference Example 1 to prepare a diphenyl carbonate containing 2.3% by mass or 11% by mass of iron as a metallic atom, or diphenyl carbonate of Reference Example 1 was isolated by distillation by a conventionally known method to make the amount of iron contained as a metallic atom be 0.0009 ppm by mass. Each amino acid was used in an equimolar amount relative to lysine used in Example 1.

Operations were conducted under conditions described in Example 1, and a gas phase component was condensed and collected. The collected liquid was analyzed by 1H-NMR and 13C-NMR, and, as a result of which, it was confirmed that the collected liquid was lysine ester triisocyanate. The yield based on lysine β-aminoethyl ester dihydrochloride was 68%. When continuous operations were conducted for 10 days, no adhesion was confirmed on the wall surface of the thin-film evaporator. In the case where arginine was used, the arginine was decomposed to ornithine by a conventionally known method to be used. In the case where glutamine or asparagine was used, the glutamine or the asparagine was hydrolyzed to glutamic acid or asparaginic acid, respectively, by a conventionally known method.

Example 90

When the thermal decomposition step in Example 5 was conducted continuously for 200 days, a small amount of adhesion was confirmed on the wall surface of the thin-film distillation equipment 701. Glutamine was hydrolyzed to glutamic acid by a conventionally known method to be used.

Example 91

The thin-film distillation equipment 701 in which the accumulation of the adhesion was confirmed in Example 90 was subjected to a washing step. The thermal decomposition operation was stopped, the thin-film distillation equipment 701 was heated at 180° C., and the internal pressure of the thin-film distillation equipment 701 was made to be atmospheric pressure under a nitrogen atmosphere. 2,6-Diphenol was supplied from a line 78 at approximately 1200 g/hr, and the washing liquid was extracted from a line 72, and then collected through the cooling equipment 703 and a line 79 in a storage tank 750. As a result of the operation conducted for 1 hour, no adhesion was confirmed in the thin-film distillation equipment 701. The glutamine was hydrolyzed to a glutamic acid by a conventionally known method.

Examples 92 to 101

The same operations as those in Example 91 were conducted, except that a washing solvent shown in Table 12 was used and a step of removing adhesion adhered in the wall surface of a thin-film evaporator 701 used in the thermal decomposition step was conducted. Results are shown in able 12 shown below. In the item "adhesion after washing operation" in the table, the term "absence" represents a result in which the adhesion was eliminated by the washing operation, and the term "presence" represents a result in which the adhesion was not eliminated by the washing operation. The glutamine was hydrolyzed to a glutamic acid by a conventionally known method.

Comparative Example 1

Although the same operations as those in Example 5 were conducted, except that triethylamine was not used in the carbamation step, the corresponding carbamic acid ester was obtained in only a trace amount, and the operation was stopped. The glutamine was hydrolyzed to a glutamic acid by a conventionally known method.

TABLE 9

| | Raw material of amino acid derivative | | | | Carbonic acid ester | | | | Result of carbamation reaction | | | Adhesion in thin film distillation equipment |
|---|---|---|---|---|---|---|---|---|---|---|---|---|
| | Amino acid | $NH_2$ group number | COOH group number | Alcohol | Abbreviation | Metallic component in carbonic acid ester | Metallic amount (ppm by mass) | Base | Esterification efficiency (%) | Carbamation yield (%) | Thermal decomposition yield (%) | by thermal decomposition of carbamate After 10 days |
| Example 58 | Lysine | 2 | 1 | Monoethanolamine | DBC | Fe | 22 | Triethylamine | 80 | 80 | 64 | Absence |
| Example 59 | Lysine | 2 | 1 | Monoethanolamine | DMC | Fe | 22 | Triethylamine | 80 | 80 | 61 | Absence |
| Example 60 | Arginine | 2 | 1 | Monoethanolamine | DBC | Fe | 22 | Triethylamine | 71 | 80 | 64 | Absence |
| Example 61 | Arginine | 2 | 1 | Monoethanolamine | DMC | Fe | 22 | Triethylamine | 71 | 85 | 62 | Absence |
| Example 62 | Asparagine | 2 | 1 | Monoethanolamine | DBC | Fe | 22 | Triethylamine | 77 | 81 | 64 | Absence |
| Example 63 | Asparagine | 2 | 1 | Monoethanolamine | DMC | Fe | 22 | Triethylamine | 77 | 76 | 62 | Absence |
| Example 64 | Glutamine | 2 | 1 | Monoethanolamine | DBC | Fe | 22 | Triethylamine | 74 | 80 | 63 | Absence |
| Example 65 | Glutamine | 2 | 1 | Monoethanolamine | DMC | Fe | 22 | Triethylamine | 74 | 77 | 62 | Absence |
| Example 66 | Lysine | 2 | 1 | Monoethanolamine | DPC | Fe | 22 | Pyridine | 78 | 85 | 70 | Absence |
| Example 67 | Lysine | 2 | 1 | Monoethanolamine | DPC | Fe | 22 | Imidazole | 80 | 90 | 70 | Absence |
| Example 68 | Lysine | 2 | 1 | Monoethanolamine | DPC | Fe | 22 | Potassium carbonate | 76 | 76 | 70 | Absence |
| Example 69 | Arginine | 2 | 1 | Monoethanolamine | DPC | Fe | 22 | Pyridine | 77 | 88 | 68 | Absence |
| Example 70 | Arginine | 2 | 1 | Monoethanolamine | DPC | Fe | 22 | Imidazole | 78 | 93 | 69 | Absence |
| Example 71 | Arginine | 2 | 1 | Monoethanolamine | DPC | Fe | 22 | Potassium carbonate | 74 | 78 | 67 | Absence |
| Example 72 | Asparagine | 2 | 1 | Monoethanolamine | DPC | Fe | 22 | Pyridine | 71 | 85 | 69 | Absence |

TABLE 9-continued

| | Raw material of amino acid derivative | | | | Carbonic acid ester | | | | Result of carbamation reaction | | | Adhesion in thin film distillation equipment by thermal decomposition of carbamate After 10 days |
|---|---|---|---|---|---|---|---|---|---|---|---|---|
| | Amino acid | $NH_2$ group number | COOH group number | Alcohol | Abbreviation | Metallic component in carbonic acid ester | Metallic amount (ppm by mass) | Base | Esterification efficiency (%) | Carbamation yield (%) | Thermal decomposition yield (%) | |
| Example 73 | Asparagine | 2 | 1 | Monoethanol amine | DPC | Fe | 22 | Imidazole | 73 | 93 | 68 | Absence |
| Example 74 | Asparagine | 2 | 1 | Monoethanol amine | DPC | Fe | 22 | Potassium carbonate | 71 | 72 | 66 | Absence |
| Example 75 | Glutamine | 2 | 1 | Monoethanol amine | DPC | Fe | 22 | Pyridine | 74 | 82 | 64 | Absence |
| Example 76 | Glutamine | 2 | 1 | Monoethanol amine | DPC | Fe | 22 | Imidazole | 72 | 95 | 66 | Absence |
| Example 77 | Glutamine | 2 | 1 | Monoethanol amine | DPC | Fe | 22 | Potassium | 71 | 70 | 65 | Absence |

TABLE 10

| | Raw material of amino acid derivative | | | | Carbonic acid ester | | | | Result of carbamation reaction | | | Adhesion in thin film distillation equipment by thermal decomposition of carbamate After 10 days |
|---|---|---|---|---|---|---|---|---|---|---|---|---|
| | Amino acid | $NH_2$ group number | COOH group number | Alcohol | Abbreviation | Metallic component in carbonic acid ester | Metallic amount | Base | Esterification efficiency (%) | Carbamation yield (%) | Thermal decomposition yield (%) | |
| Example 78 | Lysine | 2 | 1 | Monoethanol amine | DPC | Fe | 2.3 % by mass | Triethylamine | 80 | 85 | 66 | Absence |
| Example 79 | Lysine | 2 | 1 | Monoethanol amine | DPC | Fe | 11 % by mass | Triethylamine | 80 | 80 | 2 | Absence |
| Example 80 | Lysine | 2 | 1 | Monoethanol amine | DPC | Fe | 0.0009 ppm by mass | Triethyl amine | 80 | 71 | 50 | Absence |
| Example 81 | Arginine | 2 | 1 | Monoethanol amine | DPC | Fe | 2.3 % by mass | Triethylamine | 71 | 88 | 65 | Absence |
| Example 82 | Arginine | 2 | 1 | Monoethanol amine | DPC | Fe | 11 % by mass | Triethylamine | 71 | 72 | 3 | Absence |
| Example 83 | Arginine | 2 | 1 | Monoethanol amine | DPC | Fe | 0.0009 ppm by mass | Triethylamine | 71 | 80 | 49 | Absence |
| Example 84 | Asparagine | 2 | 1 | Monoethanol amine | DPC | Fe | 2.3 % by mass | Triethylamine | 77 | 89 | 64 | Absence |
| Example 85 | Asparagine | 2 | 1 | Monoethanol amine | DPC | Fe | 11 % by mass | Triethylamine | 77 | 72 | 2 | Absence |
| Example 86 | Asparagine | 2 | 1 | Monoethanol amine | DPC | Fe | 0.0009 ppm by mass | Triethylamine | 77 | 74 | 51 | Absence |
| Example 87 | Glutamine | 2 | 1 | Monoethanol amine | DPC | Fe | 2.3 % by mass | Triethylamine | 74 | 89 | 62 | Absence |
| Example 88 | Glutamine | 2 | 1 | Monoethanol amine | DPC | Fe | 11 % by mass | Triethylamine | 74 | 74 | 2 | Absence |
| Example 89 | Glutamine | 2 | 1 | Monoethanol amine | DPC | Fe | 0.0009 ppm by mass | Triethylamine | 74 | 70 | 52 | Absence |

TABLE 11

| Amino acid | NH₂ group number | COOH group number | Alcohol | Abbreviation | Metallic component in carbonic acid ester | Metallic amount (ppm by mass) | Base | Esterification efficiency (%) | Carbamation yield (%) | Thermal decomposition yield (%) | Adhesion After 10 days | Adhesion After 200 days |
|---|---|---|---|---|---|---|---|---|---|---|---|---|
| Example 90 Glutamine | 2 | 1 | Monoethanol amine | DPC | Fe | 22 | Triethyl-amine | 80 | 87 | 70 | Absence | Presence |
| Example 91 Glutamine | 2 | 1 | Monoethanol amine | DPC | Fe | 22 | Triethyl-amine | 80 | 87 | 70 | Absence | Presence |
| Example 92 Glutamine | 2 | 1 | Monoethanol amine | DPC | Fe | 22 | Triethyl-amine | 80 | 87 | 70 | Absence | Presence |
| Example 93 Glutamine | 2 | 1 | Monoethanol amine | DPC | Fe | 22 | Triethyl-amine | 80 | 87 | 70 | Absence | Presence |
| Example 94 Glutamine | 2 | 1 | Monoethanol amine | DPC | Fe | 22 | Triethyl-amine | 80 | 87 | 70 | Absence | Presence |
| Example 95 Glutamine | 2 | 1 | Monoethanol amine | DPC | Fe | 22 | Triethyl-amine | 80 | 87 | 70 | Absence | Presence |
| Example 96 Glutamine | 2 | 1 | Monoethanol amine | DPC | Fe | 22 | Triethyl-amine | 80 | 87 | 70 | Absence | Presence |
| Example 97 Glutimine | 2 | 1 | Monoethanol amine | DPC | Fe | 22 | Triethyl-amine | 80 | 87 | 70 | Absence | Presence |
| Example 98 Glutamine | 2 | 1 | Monoethanol amine | DPC | Fe | 22 | Triethyl-amine | 80 | 87 | 70 | Absence | Presence |
| Example 99 Glutamine | 2 | 1 | Monoethanol amine | DPC | Fe | 22 | Triethyl-amine | 80 | 82 | 70 | Absence | Presence |
| Example 100 Glutamine | 2 | 1 | Monoethanol amine | DPC | Fe | 22 | Triethyl-amine | 80 | 85 | 70 | Absence | Presence |
| Example 101 Glutamine | 2 | 1 | Monoethanol amine | DPC | Fe | 22 | Triethyl-amine | 80 | 83 | 70 | Absence | Presence |
| Comparative Example 1 Glutamine | 2 | 1 | Monoethanol amine | DPC | Fe | 22 | Not used | 80 | (Interrupted) | (Interrupted) | — | — |

TABLE 12

| | Temperature of thin film distillation equipment | Washing solvent | Amount of supplied washing solvent | Washing time | Adhesion after washing step |
|---|---|---|---|---|---|
| Example 91 | 200° C. | 2.6-Dimethyl phenol | 1000 g/Hr | 2 Hours | Absence |
| Example 92 | 210° C. | 2,4,6-Trimethyl phenol | 800 g/Hr | 2 Hours | Absence |
| Example 93 | 250° C. | 2-Phenyl phenol | 1000 g/Hr | 3 Hours | Absence |
| Example 94 | 280° C. | 2,4-(α,α-Dimethyl benzyl) phenol | 1200 g/Hr | 1 Hour | Absence |
| Example 95 | 200° C. | 4-Ethoxy phenol | 1100 g/Hr | 2 Hours | Absence |
| Example 96 | 270° C. | 4-Dodecyl phenol | 1300 g/Hr | 1 Hour | Absence |
| Example 97 | 200° C. | Salicylic acid | 800 g/Hr | 2 Hours | Absence |
| Example 98 | 220° C. | Benzoic acid | 800 g/Hr | 4 Hours | Absence |
| Example 99 | 200° C. | n-Dodecane | 1000 g/Hr | 4 Hours | Presence |
| Example 100 | 200° C. | Naphthalene | 1000 g/Hr | 4 Hours | Presence |
| Example 101 | 180° C. | 1-Phenyl ethanol | 1000 g/Hr | 4 Hours | Presence |

INDUSTRIAL APPLICABILITY

According to the present invention, the production method of the carbamic acid ester, by which the carbamation reaction efficiency and the separation and collection efficiency are improved, and the isocyanate production method using the carbamic acid ester are provided.

DESCRIPTION OF THE REFERENCE NUMERALS

- 1, 2, 3, 4, 5, 6, 7, 8, 9, 10, 11, 12, 13, 14, 15, 16, 17, 21, 22, 23, 24, 25, 31, 32, 33, 34, 35, 41, 42, 43, 44, 45, 51, 52, 53, 54, 55, 61, 62, 63, 64, 65, 71, 72, 73, 74, 75, 76, 77, 78, 79: line
- 101: distillation column
- 102: tower-type reactor
- 103: thin-film distillation tank
- 104: autoclave
- 105: carbon removing tank
- 106: thin-film distillation equipment
- 107: distillation column
- 111, 112, 117, 204, 304, 404, 504, 604: reboiler
- 121, 123, 126, 127, 203, 303, 403, 603, 702, 705: condenser
- 201, 301, 401, 501, 601: preheater
- 703, 706: cooling equipment
- 205, 206, 305, 306, 405, 406, 506, 605, 606, 700, 710, 720, 730, 740, 750: storage tank
- 202, 302, 402, 502, 602: continuous multistage distillation column
- 701, 704: thin-film distillation equipment

The invention claimed is:

1. A production method of a carbamic acid ester derived from a carbonic acid ester, comprising supplying the carbonic acid ester, an inorganic acid salt of an amino acid derivative, and a basic compound to a carbamation reactor to allow reaction to proceed, wherein the carbonic acid ester comprises 0.001 ppm by mass to 10% by mass of a metallic atom, relative to a total mass of the carbonic acid ester.

2. The production method of a carbamic acid ester according to claim 1, wherein the amino acid derivative is an amino acid derivative of formula (A-1) or (A-2):

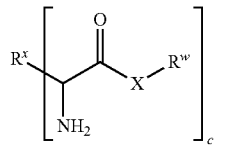
(A-1)

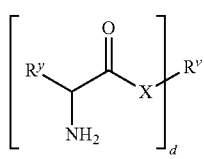
(A-2)

wherein, $R^x$ represents an aliphatic group or an aromatic group, $R^w$, $R^y$, and $R^v$ each independently represent an aliphatic group, an aromatic group, or a hydrogen atom, X represents an oxygen atom, or a secondary amino group (—NH—), c represents 2 or 3, and d represents an integer of 1 to 4.

3. The production method of a carbamic acid ester according to claim 2, wherein the amino acid derivative is an amino acid ester, the production method further comprising a production step of the inorganic acid salt of the amino acid ester by reacting an amino acid and a compound having an alcoholic hydroxy group in a presence of an inorganic acid.

4. The production method of a carbamic acid ester according to claim 3, wherein the basic compound is an organic amine.

5. The production method of a carbamic acid ester according to claim 4, wherein the carbonic acid ester comprises 0.001 ppm by mass to 5% by mass of a metallic atom, relative to a total mass of the carbonic acid ester.

6. The production method of a carbamic acid ester according to claim 5, wherein the inorganic acid salt of the amino acid derivative is supplied to the carbamation reactor in a liquid state.

7. An isocyanate production method comprising:
a preparation step in which a carbamic acid ester is prepared by a production method of a carbamic acid ester of claim 1; and
a thermal decomposition step in which the carbamic acid ester is subjected to a thermal decomposition reaction to obtain an isocyanate.

8. The isocyanate production method according to claim 7, wherein the thermal decomposition step is conducted in a thermal decomposition reactor, the isocyanate production method further comprising a washing step in which, after the thermal decomposition step, the thermal decomposition reactor is washed with an acid.

9. The isocyanate production method according to claim 8, wherein the thermal decomposition reaction is conducted in a liquid phase.

10. The production method of a carbamic acid ester according to claim 1, wherein the carbonic acid ester is a compound of formula (1):

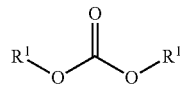
(1)

wherein $R^1$ each independently represents a C1-20 aliphatic hydrocarbon group, or, a C6-20 aromatic group.

11. The production method of a carbamic acid ester according to claim 1, wherein the metallic atom is selected from the group consisting of iron, cobalt, nickel, zinc, tin, copper, and titanium.

12. The production method of a carbamic acid ester according to claim 2, wherein the amino acid derivative is the amino acid derivative of formula (A-1), and the amino acid derivative of formula (A-1) includes a compound of the following formula:

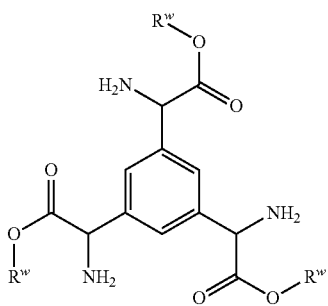

wherein $R^w$ is a C1-C6 alkyl group.

13. The production method of a carbamic acid ester according to claim 2, wherein the amino acid derivative is the amino acid derivative of formula (A-1), and the amino acid derivative of formula (A-1) includes a compound of the following formula:

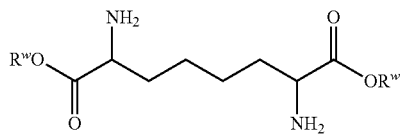

wherein Fr is a C1-C6 alkyl group.

14. The production method of a carbamic acid ester according to claim 2, wherein the amino acid derivative is the amino acid derivative of formula (A-1), and the amino acid derivative of formula (A-1) includes a compound of the following formula:

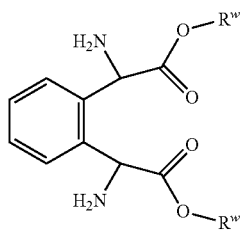

wherein $R^w$ is a C1-C6 alkyl group.

15. The production method of a carbamic acid ester according to claim 2, wherein the amino acid derivative is the amino acid derivative of formula (A-2), and the amino acid derivative of formula (A-2) includes a compound of the following formulae (A-3):

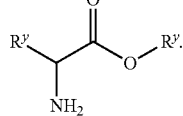

(A-3)

16. The production method of a carbamic acid ester according to claim 2, wherein the amino acid derivative is the amino acid derivative of formula (A-2), and the amino acid derivative of formula (A-2) includes a compound of the following formulae (A-4):

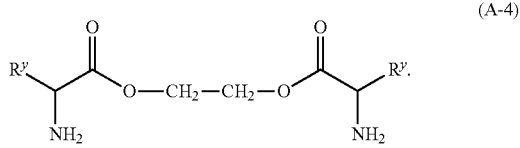

(A-4)

17. The production method of a carbamic acid ester according to claim 2, wherein the amino acid derivative is the amino acid derivative of formula (A-2), and the amino acid derivative of formula (A-2) includes a compound of the following formulae (A-5):

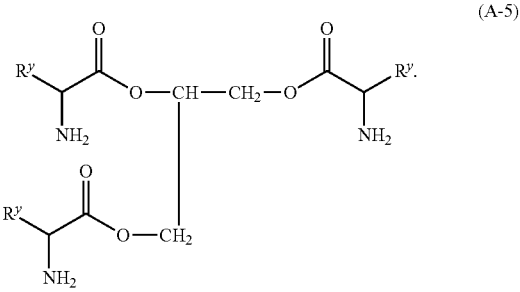

(A-5)

18. The production method of a carbamic acid ester according to claim 2, wherein the amino acid derivative is the amino acid derivative of formula (A-2), and the amino acid derivative of formula (A-2) includes a compound of the following formulae (A-6):

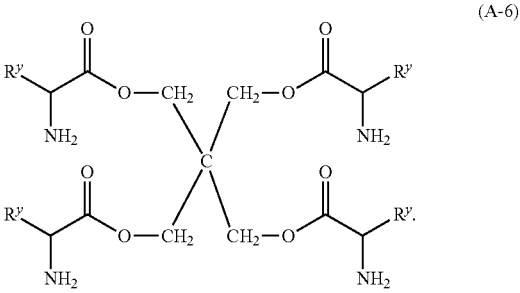

(A-6)

* * * * *